US012788432B2

(12) United States Patent
Buck et al.

(10) Patent No.: US 12,788,432 B2
(45) Date of Patent: Nov. 10, 2026

(54) CATHETER ASSEMBLY LOCK

(71) Applicant: Boston Scientific Scimed, Inc., Maple Grove, MN (US)

(72) Inventors: Eric Daniel Buck, Shoreview, MN (US); Jacob Clark Ruprecht, Menlo Park, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 403 days.

(21) Appl. No.: 18/393,258

(22) Filed: Dec. 21, 2023

(65) Prior Publication Data

US 2024/0225691 A1 Jul. 11, 2024

Related U.S. Application Data

(60) Provisional application No. 63/478,866, filed on Jan. 6, 2023.

(51) Int. Cl.

| | |
|---|---|
| ***A61B 17/34*** | (2006.01) |
| ***A61B 5/283*** | (2021.01) |
| ***A61B 18/14*** | (2006.01) |
| ***A61M 25/00*** | (2006.01) |
| ***A61M 25/06*** | (2006.01) |
| ***A61M 39/28*** | (2006.01) |

(52) U.S. Cl.

CPC .......... *A61B 17/3415* (2013.01); *A61B 5/283* (2021.01); *A61B 2017/347* (2013.01); *A61B 18/1492* (2013.01); *A61M 2025/0006* (2013.01); *A61M 2025/0681* (2013.01); *A61M 39/28* (2013.01)

(58) Field of Classification Search

CPC ......... A61B 17/3415; A61B 2017/347; A61M 39/28; A61M 2025/0681

See application file for complete search history.

(56) References Cited

U.S. PATENT DOCUMENTS

| | | | | |
|---|---|---|---|---|
| 5,279,597 A * | 1/1994 | Dassa | ................ | A61M 25/0111 604/165.04 |
| 5,348,537 A | 9/1994 | Wiesner | | |
| 5,429,616 A * | 7/1995 | Schaffer | .............. | A61M 39/284 604/250 |
| 9,339,631 B2 | 5/2016 | Graham | | |

(Continued)

FOREIGN PATENT DOCUMENTS

EP 1513454 B1 3/2005

OTHER PUBLICATIONS

International Search Report and Written Opinion issued in PCT/US2023/085542, mailed Apr. 30, 2024.

*Primary Examiner* — Bradley J Osinski

(74) *Attorney, Agent, or Firm* — Nelson Mullins Riley & Scarborough LLP

(57) ABSTRACT

A medical device for use with a catheter assembly including an elongated catheter coaxially disposed within a sheath is disclosed. The medical device includes a deformable tube having a proximal end, a distal end, an outer wall with an outer diameter, and an inner wall forming an axial lumen. The distal end attaches to the sheath, and the proximal end receives the catheter into the lumen. The medical device also includes a opposing paddles disposed against the outer wall, each of the opposing paddles having a generally planar lock region to be disposed against outer wall at the outer diameter, the lock surface tangential to the deformable tube.

20 Claims, 17 Drawing Sheets

(56) References Cited

U.S. PATENT DOCUMENTS

| | | | |
|---|---|---|---|
| 2014/0350471 | A1 | 11/2014 | Schultz |
| 2017/0281920 | A1 | 10/2017 | Furnish |
| 2020/0345904 | A1 | 11/2020 | Casey |
| 2021/0069473 | A1 | 3/2021 | Marass |

* cited by examiner

CATHETER ASSEMBLY LOCK

CROSS REFERENCE TO RELATED APPLICATION

The present application claims the benefit and priority to U.S. Provisional Patent Application Ser. No. 63/478,866, filed Jan. 6, 2023, which is incorporated herein in its entirety.

TECHNICAL FIELD

The present disclosure relates generally to medical systems and methods using catheter assemblies. More specifically, the present disclosure relates to medical systems and methods for locking catheter assemblies in position within a patient during procedures.

BACKGROUND

Medical devices in the form of catheter systems are widely used in various medical procedures to access remote anatomical locations or deploy therapeutic devices. For example, electrophysiological procedures involve guiding catheter assemblies into the heart and tracking the location of the catheter assemblies with respect to the heart. Catheter ablation is a minimally invasive electrophysiological procedure to treat a variety of heart conditions such as supraventricular and ventricular arrhythmia. Cardiac mapping via catheters is another minimally invasive electrophysiological procedure to identify temporal and spatial electrical potentials during a heart rhythm. Catheter assemblies, including catheter assemblies in electrophysiological procedures, can include a plurality of catheter elements such as catheters, sheaths, guidewires, and needles. For instance, a catheter assembly can include an elongated catheter within an elongated sheath. Access to the patient's heart can be obtained through a vessel, such as a peripheral artery or vein via a large bore sheath or introducer sheath. Once access to the vessel is obtained, the catheter assembly can be navigated to within the patient's heart, and the catheter can be selectively deployed from within the sheath.

SUMMARY

In Example 1, a medical device for use with a catheter assembly including an elongated catheter coaxially disposed within a sheath. The medical device includes a deformable tube having a proximal end, a distal end, an outer wall with an outer diameter, and an inner wall forming an axial lumen, the distal end configured to attach to the sheath, the proximal end configured to receive the catheter into the lumen. The medical device also includes a plurality of opposing paddles disposed against the outer wall, each of the opposing paddles having a generally planar lock region configured to be disposed against outer wall at the outer diameter, the lock surface disposed tangentially to the deformable tube, the plurality of opposing paddles laterally movable with respect to the deformable tube along the outer diameter. The medical device having a first compressed state wherein the catheter is coaxially disposed within the sheath and the opposing paddles are releasably urged against the deformable tube at the outer diameter to collapse the deformable tube to hold the catheter in place with respect to the sheath and deformable tube, the collapsed deformable tube to form an elongated opening along the inner wall and the catheter. The medical device having a second compressed state wherein the catheter is not coaxially disposed within the sheath and removed from the deformable tube and the opposing paddles are releasably urged against the deformable tube at the outer diameter to collapse the deformable tube and seal the lumen.

In Example 2, the medical device of Example 1, wherein the catheter assembly is incorporated into the medical device.

In Example 3, the medical device of any of Examples 1-2, wherein the catheter assembly is configured to perform an irreversible electroporation.

In Example 4, the medical device of any of Example 1-3, and further comprising a nominal state wherein the catheter is coaxially disposed within the sheath, and the catheter is movable with respect to the sheath and the deformable tube.

In Example 5, the medical device of Example 4, wherein the inner wall includes a circular cross section in the nominal state.

In Example 6, the medical device of Example 5, wherein the lock regions include a height and the inner wall includes a circumference, and wherein the height is at least half the circumference.

In Example 7, the medical device of any of Examples 4-5, wherein the inner wall includes an ovalized cross section in the first compressed state.

In Example 8, the medical device of any of Examples 1-7, wherein the plurality of opposing paddles includes two opposing paddles.

In Example 9, the medical device of Example 8, wherein the lock regions are generally parallel to each other.

In Example 10, the medical device of any of Examples 1-9, wherein lock regions form an overlapping region on the deformable tube.

In Example 11, the medical device of Example 10, wherein the inner wall associated with the overlapping region pinches the catheter in the first compressed state.

In Example 12, the medical device of any of Examples 10-11, wherein the inner wall associated with the overlapping region seals the lumen in the second compressed state.

In Example 13, the medical device of any of Examples 10-12, wherein the proximal end and distal end are spaced apart from the overlapping region.

In Example 14, the medical device of any of Examples 1-13, wherein the proximal end includes a proximal hub configured to guide the catheter into the lumen, and the distal end includes a distal hub configured to attach to the sheath.

In Example 15, the medical device of any of Examples 1-14, and further comprising a drive mechanism operably coupled to the plurality of paddles, the drive mechanism configured to laterally move the plurality of opposing paddles with respect to the deformable tube.

In Example 16, a medical device for use with a catheter assembly including an elongated catheter coaxially disposed within a sheath. The medical device includes a deformable tube having a proximal end, a distal end, an outer wall with an outer diameter, and an inner wall forming an axial lumen, the distal end configured to attach to the sheath, the proximal end configured to receive the catheter into the lumen. The medical device also includes a plurality of opposing paddles disposed against the outer wall, each of the opposing paddles having a generally planar lock region configured to be disposed against outer wall at the outer diameter, the lock surface disposed tangentially to the deformable tube, the plurality of opposing paddles laterally movable with respect to the deformable tube along the outer diameter. The medical device having a first compressed state wherein the catheter is coaxially disposed within the sheath and the opposing paddles are releasably urged against the deformable tube at the outer diameter to collapse the deformable tube to hold the catheter in place with respect to the sheath and deformable tube, the collapsed deformable tube to form an elongated opening along the inner wall and the catheter. The medical device having a second compressed state wherein the catheter is not coaxially disposed within the sheath and removed from the deformable tube and the opposing paddles are releasably urged against the deformable tube at the outer diameter to collapse the deformable tube and seal the lumen.

In Example 17, the medical device of Example 16, and further comprising a nominal state wherein the catheter is coaxially disposed within the sheath, and the catheter is movable with respect to the sheath and the deformable tube.

In Example 18, the medical device of Example 17, wherein the inner wall includes a circular cross section in the nominal state.

In Example 19, the medical device of Example 18, wherein the lock regions include a height and the inner wall includes a circumference, and wherein the height is at least half the circumference.

In Example 20, the medical device of Example 18, wherein the inner wall includes an ovalized cross section in the first compressed state.

In Example 21, the medical device of Example 16, wherein lock regions form an overlapping region on the deformable tube and the proximal end and distal end are spaced apart from the overlapping region.

In Example 22, the medical device of Example 16, and further comprising a drive mechanism operably coupled to the plurality of paddles, the drive mechanism configured to laterally move the plurality of opposing paddles with respect to the deformable tube.

In Example 23, the medical device of Example 16, wherein the proximal end includes a proximal hub configured to guide the catheter into the lumen, and the distal end includes a distal hub configured to attach to the sheath.

In Example 24, the medical device of Example 16, wherein the plurality of opposing paddles includes two opposing paddles, and wherein the lock regions are generally parallel to each other.

In Example 25, a medical system comprising a catheter assembly having an elongated catheter coaxially disposable within a sheath and a locking mechanism. The locking mechanism comprising a deformable tube and a plurality of opposing paddles. The deformable tube having a proximal end, a distal end, an outer wall with an outer diameter, and an inner wall forming an axial lumen, the distal end configured to attach to the sheath, the proximal end configured to receive the catheter into the lumen. The plurality of opposing paddles disposed against the outer wall, each of the opposing paddles having a generally planar lock region configured to be disposed against outer wall at the outer diameter, the lock surface disposed tangentially to the deformable tube, the plurality of opposing paddles laterally movable with respect to the deformable tube along the outer diameter. The medical system having a first compressed state wherein the catheter is coaxially disposed within the sheath and the opposing paddles are releasably urged against the deformable tube at the outer diameter to collapse the deformable tube to hold the catheter in place with respect to the sheath and deformable tube, the collapsed deformable tube to form an elongated opening along the inner wall and the catheter. The medical system having a second compressed state wherein the catheter is not coaxially disposed within the sheath and removed from the deformable tube and the opposing paddles are releasably urged against the deformable tube at the outer diameter to collapse the deformable tube and seal the lumen.

In Example 26, the medical system of Example 25, wherein the catheter assembly is configured to perform an irreversible electroporation.

In Example 27, the medical system of Example 25, and further comprising a nominal state wherein the catheter is coaxially disposed within the sheath, and the catheter is movable with respect to the sheath and the deformable tube.

In Example 28, the medical system of Example 25, and further comprising a drive mechanism operably coupled to the plurality of paddles, the drive mechanism configured to laterally move the plurality of opposing paddles with respect to the deformable tube.

In Example 29, a method for use with catheter assembly having an elongated catheter coaxially disposable within a sheath. A medical device is provided. The medical device includes a deformable tube having a proximal end, a distal end, an outer wall with an outer diameter, and an inner wall forming an axial lumen, the distal end configured to attach to the sheath, the proximal end configured to receive the catheter into the lumen. The medical device also includes a plurality of opposing paddles disposed against the outer wall, each of the opposing paddles having a generally planar lock region configured to be disposed against outer wall at the outer diameter, the lock surface disposed tangentially to the deformable tube, the plurality of opposing paddles laterally movable with respect to the deformable tube along the outer diameter. The catheter is coaxially disposed within the sheath. The opposing paddles are releasably urged against the deformable tube at the outer diameter to collapse the deformable tube to hold the catheter in place with respect to the sheath and deformable tube, the collapsed deformable tube to form an elongated opening along the inner wall and the catheter. The catheter is removed from the deformable tube. The opposing paddles are releasably urged against the deformable tube at the outer diameter to collapse the deformable tube and seal the lumen.

In Example 30, the method of Example 29, and further including flowing a fluid into the elongated opening.

In Example 31, the method of Example 30, wherein providing the medical device includes providing the deformable tube having an inner wall with a circular cross section, and wherein holding the catheter in place with respect to the sheath includes ovalizing the cross section to form the elongated opening.

In Example 32, the method of Example 29, including forming an overlapping region on the deformable tube In Example 33, the method of Example 32, wherein holding the catheter in place with respect to the sheath includes pinching the catheter with the inner wall associated with the overlapping region.

In Example 34, the method of Example 32, wherein collapsing the deformable tube and sealing the lumen includes collapsing the deformable tube at the overlapping region.

In Example 35, the method of Example 29, wherein providing the medical device includes providing a proximal hub attached to the proximal end, and further including guiding the catheter into lumen via the proximal hub.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
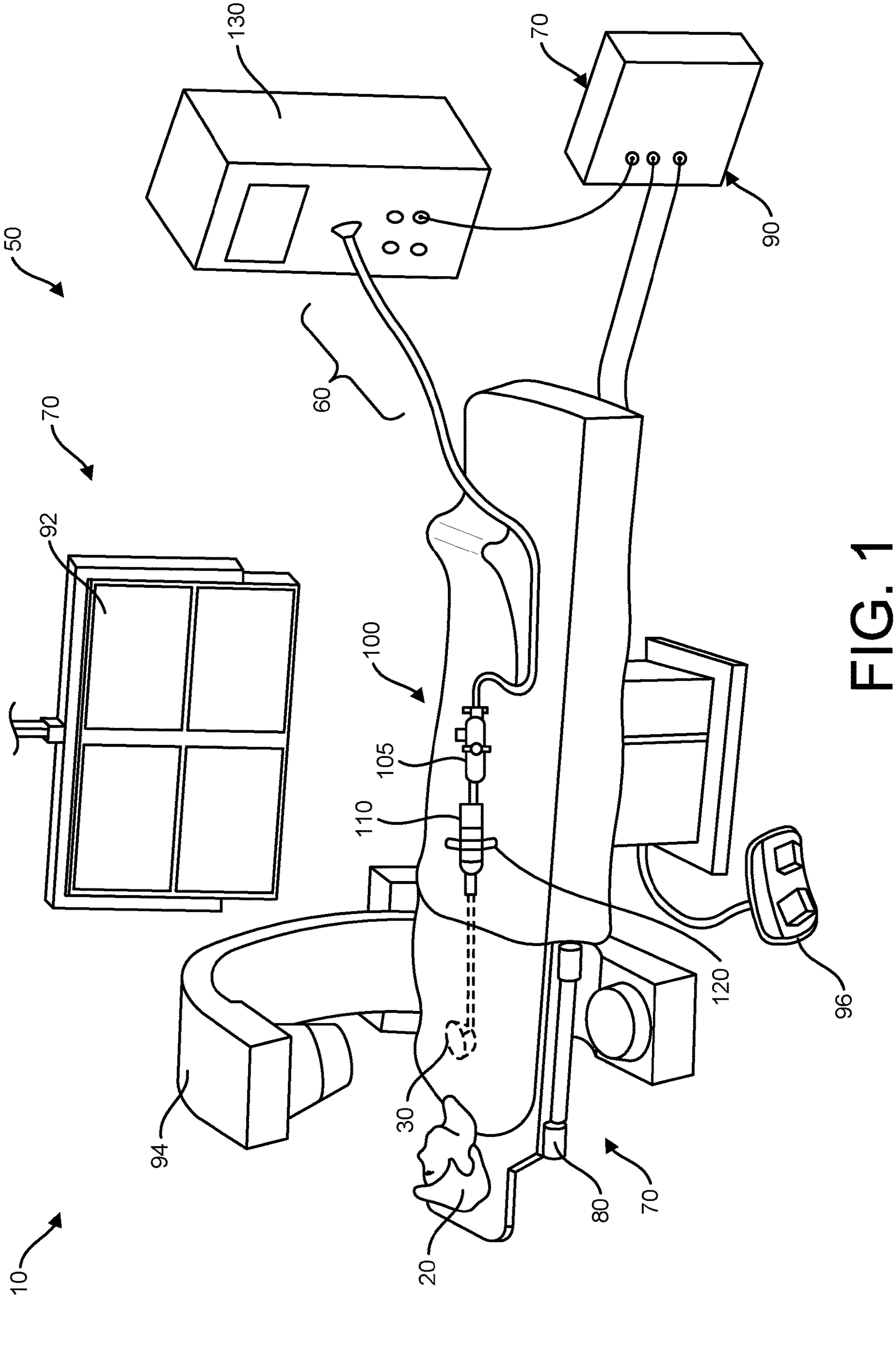
FIG. 1 is a diagram illustrating an example clinical setting for treating a patient, and for treating a heart of the patient, the example clinical setting having an example electrophysiology system.

While the disclosure is amenable to various modifications and alternative forms, specific embodiments have been shown by way of example in the drawings and are described in detail below. The intention, however, is not to limit the disclosure to the particular embodiments described. Rather, the disclosure is intended to cover all modifications, equivalents, and alternatives falling within the scope of the disclosure as defined by the appended claims.

DETAILED DESCRIPTION

For purposes of promoting an understanding of the principles of the present disclosure, reference is now made to the examples illustrated in the drawings, which are described below. The illustrated examples disclosed herein are not intended to be exhaustive or to limit the disclosure to the precise form disclosed in the following detailed description. Rather, these exemplary embodiments were chosen and described so that others skilled in the art may use their teachings. It is not beyond the scope of this disclosure to have a number (e.g., all) of the features in an example used across all examples. Thus, no one figure should be interpreted as having any dependency or requirement related to any single component or combination of components illustrated therein. Additionally, various components depicted in a figure may be, in examples, integrated with various ones of the other components depicted therein (or components not illustrated), all of which are considered to be within the ambit of the present disclosure.

Examples of electrophysiological procedures and systems in which electroanatomical mapping systems and cardiac ablation systems that employ catheter assemblies are described in this disclosure with electrophysiological testing and ablation systems for illustration. Ablation procedures are used to treat many different conditions in patients. Ablation can be used to treat cardiac arrhythmias, benign tumors, cancerous tumors, and to control bleeding during surgery. Usually, ablation is accomplished through thermal ablation techniques including radio-frequency (RF) ablation and cryoablation. In RF ablation, a probe is inserted into the patient and radio frequency waves are transmitted through the probe to the surrounding tissue. The radio frequency waves generate heat, which destroys surrounding tissue and cauterizes blood vessels. In cryoablation, a hollow needle or cryoprobe is inserted into the patient and cold, thermally conductive fluid is circulated through the probe to freeze and kill the surrounding tissue. RF ablation and cryoablation techniques can indiscriminately kill tissue through cell necrosis, which may damage or kill otherwise healthy tissue, such as tissue in the esophagus, phrenic nerve cells, and tissue in the coronary arteries.

Another ablation technique uses electroporation. In electroporation, or electro-permeabilization, an electrical field is applied to cells to increase the permeability of the cell membrane. The electroporation can be reversible or irreversible, depending on the strength and duration of the electric field. If the electroporation is reversible, the temporarily increased permeability of the cell membrane can be used to introduce chemicals, drugs, or deoxyribonucleic acid (DNA) into the cell, prior to the cell healing and recovering. Tissue recovery can occur over minutes, hours, or days after the ablation is completed. If the electroporation is irreversible, the affected cells are killed, such as via form of cell death, such as perhaps programmed cell death through apoptosis for example, or such as traumatic cell death through necrosis for example.

Irreversible electroporation can be used as a nonthermal ablation technique. In irreversible electroporation, trains of short, high voltage pulses are used to generate electric fields that are strong enough to kill cells. In ablation of cardiac tissue, irreversible electroporation can be a relatively safe and effective alternative to the indiscriminate killing of thermal ablation techniques, such as RF ablation and cryoablation. Irreversible electroporation can be used to kill targeted tissue, such as myocardium tissue, by using a selected electric field strength and duration that is effective to kill the targeted tissue but is not effective to permanently damage other cells or tissue, such as non-targeted myocardium tissue, red blood cells, vascular smooth muscle tissue, endothelium tissue, and nerve cells.

Such example electrophysiological procedures often involve guiding catheter assemblies into the patient's heart. Access to the patient's heart can be obtained through a vessel via an introducer sheath. Once access to the vessel is obtained, the catheter assembly can be navigated to within the patient's heart. Other examples of procedures involving large bore sheaths are contemplated such as transcatheter aortic valve replacement, endovascular aneurysm repair, and mechanical circulatory support devices employ large bore access for deployment. Current use of large bore sheaths, however, include issues with air ingress during device introduction and removal. To address the issue of air ingress, clinicians employ informal methods such as high flush, aspiration, and water baths to mitigate risks of complications including air embolisms.

FIG. 1 illustrates an example clinical setting 10 for treating a patient 20, such as for treating a heart 30 of the patient 20, using an electrophysiology system 50, in accordance with the disclosure. The electrophysiology system 50 includes an ablation catheter system 60 and an electroanatomical mapping (EAM) system 70. The example catheter system 60 includes an elongated catheter assembly 100, which, in the example includes a catheter 105 within a sheath, an introducer sheath 110, a lock mechanism 120, and a console 130. The electroporation console 130 is configured to control aspects of the electroporation catheter system 60. Additionally, the catheter system 60 includes various connecting elements, such as cables, that operably connect the components of the catheter system 60 to one another and to the components of the EAM system 70. In general, the EAM system 70 includes a localization field generator 80, a mapping and navigation controller 90, and a display 92. The EAM system 70 is operable to track the location of the various components of the catheter system 60, and to generate high-fidelity three-dimensional electro-anatomical maps of the heart, including portions of the heart such as cardiac chambers of interest or other structures of interest such as the sinoatrial node or atrioventricular node from a catheter or probe equipped with sensing electrodes. In one illustrative example, the EAM system 70 can include the RHYTHMIA™ HDx mapping system marketed by Boston Scientific Corporation. One exemplary probe is the INTELLAMAP ORION™ mapping catheter marketed by Boston Scientific Corporation. Also, the clinical setting 10 can include additional equipment such as imaging equipment 94 (represented by the C-arm) and various controller elements, such as a foot controller 96, configured to allow an operator to control various aspects of the electrophysiology system 50. The clinical setting 10 may have other components and arrangements of components that are not shown in FIG. 1.

The introducer sheath 110 is operable to provide a delivery conduit through which the catheter assembly 100 can be deployed to the specific target sites within the patient's heart 30. Access to the patient's heart can be obtained through a vessel, such as a peripheral artery or vein. Once access to the vessel is obtained, the catheter assembly 100 can be navigated to within the patient's heart, such as within a chamber of the heart. The lock mechanism can be a separate component in the catheter system 60 or as a feature of another component, such as the introducer sheath 110 or other component.

The example catheter 105 includes an elongated catheter shaft and distal end configured to be deployed proximate target tissue, such as within a chamber of the patient's heart. The distal end may include a basket, balloon, spline, configured tip, or other electrode deployment mechanism. The electrode deployment mechanism includes an electrode assembly, or array, comprising of an electrode to effect treatment or to sense an effect within the heart. For example, the electrode assembly can include a plurality of spaced-apart electrodes or multiple spaced-apart sets or groups of spaced-apart electrodes. In some examples, an electrode, such as a plurality of spaced-apart electrodes, can be deployed on the catheter shaft in addition to or instead of an electrode on the electrode deployment mechanism. In one example, the plurality of electrodes can be formed of a conductive, solid-surface, biocompatible material and are spaced-apart across insulators. Each of the plurality of electrodes is electrically coupled to a corresponding elongated lead conductor that extend along the shaft to a catheter proximal end. The lead conductors can be electrically coupled to plug in the proximal region of the catheter 105, such as a plug configured to be mechanically and electrically coupled to the console 130, for example, either directly or via intermediary electrical conductors such as cabling.

In one example, the console 130 is configured to provide an electrical signal, such as a plurality of concurrent or space-apart-time electrical signals, to the electrically connected catheter 105 along lead conductors to the spaced-apart electrodes. In an example of an ablation catheter, the spaced-apart electrodes are configured to generate a selected electrical signal proximate the target tissue, based on the electrical signals from the console 130, to effect ablation.

The ablation catheter system 60 is configured to deliver energy to targeted tissue in the patient's heart 30 to create cell death in tissue, for example, rendering the tissue incapable of conducting electrical signals. An elongated catheter assembly, such as catheter assembly 100, can include a plurality of coaxially disposed catheter elements. For instance, a catheter element such as a sheath or catheter defines a longitudinal axis that passes through a centroid of a cross section of the catheter element, such as the centroid of a cross section of a catheter shaft or a centroid of a cross section of a lumen of a sheath. Coaxial disposed catheter elements include a catheter element disposed within another catheter element such that the longitudinal axes of each catheter element generally follow the same three-dimensional curve or path up to the most distal point that both are present.

The catheter elements can include a first catheter element, such as an elongated sheath, or outer catheter element in catheter assembly 100. Addition, the catheter elements can include a second catheter element, such as an elongated catheter, or inner catheter element in catheter assembly 100. The first catheter element includes an elongated lumen and the second catheter element is disposed within the lumen. For example, an outer diameter of the catheter is selected to be less than an inner diameter of the lumen in the sheath. The first and second catheter elements are movable with respect to each other along the longitudinal axis. For example, a distal end of the catheter can be manipulated to extend from the distal tip of the sheath, or the distal tip of the sheath can be retracted from the distal end of the catheter such as to expose the deployment mechanism, which can include expanding the basket. Additionally, the distal end of the catheter can be retracted from the distal tip of the sheath in the assembly 100 such as to contract the deployment mechanism or retract electrodes.

A selected electrical field can be generated with the electrodes to effect electroporation. A first electrode, or first group of electrodes, can be selected to be an anode and a different, second electrode, or second group of electrodes, can be selected to be a cathode, such that electrical fields can be generated between the anode and cathode based on signals, such as pulses, provided to the electrodes from the electroporation console 130. The console 130 provides electric pulses of different lengths and magnitudes to the electrodes on the catheter 105. The electric pulses can be provided in a continuous stream of pulses or in multiple, separate trains of pulses. Pulse parameters of interest include the number of pulses, the duty cycle of the pulses, the spacing of pulse trains, the voltage or magnitude of the pulses including the peak voltages, and the duration of the voltages. For example, the console 130 can select two or more electrodes of the electrode assembly and provides pulses to the selected electrodes to generate electric fields between the selected electrodes to provide pulsed field ablation (PFA). For example, PFA can be performed with monophasic waveforms and biphasic waveforms. Without being bound to a particular theory, electric field strengths in the range of generally 200-250 volts per centimeter (V/cm) with microsecond-scale pulse duration have been demonstrated to provide reversible electroporation in cardiac tissue. Electric field strengths at approximately 400 V/cm have been demonstrated to provide irreversible electroporation in cardiac tissue of interest, such as targeted myocardium tissue and endocardium tissue, with demonstrable sparing of red blood cells, vascular smooth muscle tissue, endothelium tissue, nerves and other non-targeted proximate tissue.

Another issue encountered during cardiac ablation involves catheter electrodes inadvertently migrating back into the elongated sheath during manipulation unbeknownst to the clinician. For instance, bipolar catheters can include shaft electrodes proximal to the electrode deployment mechanism such as a basket, and the shaft electrodes can be rendered inefficient or ineffective if inadvertently positioned within the sheath during ablation, which can lead to extended procedures or unsuccessful therapy.

Figure 2:
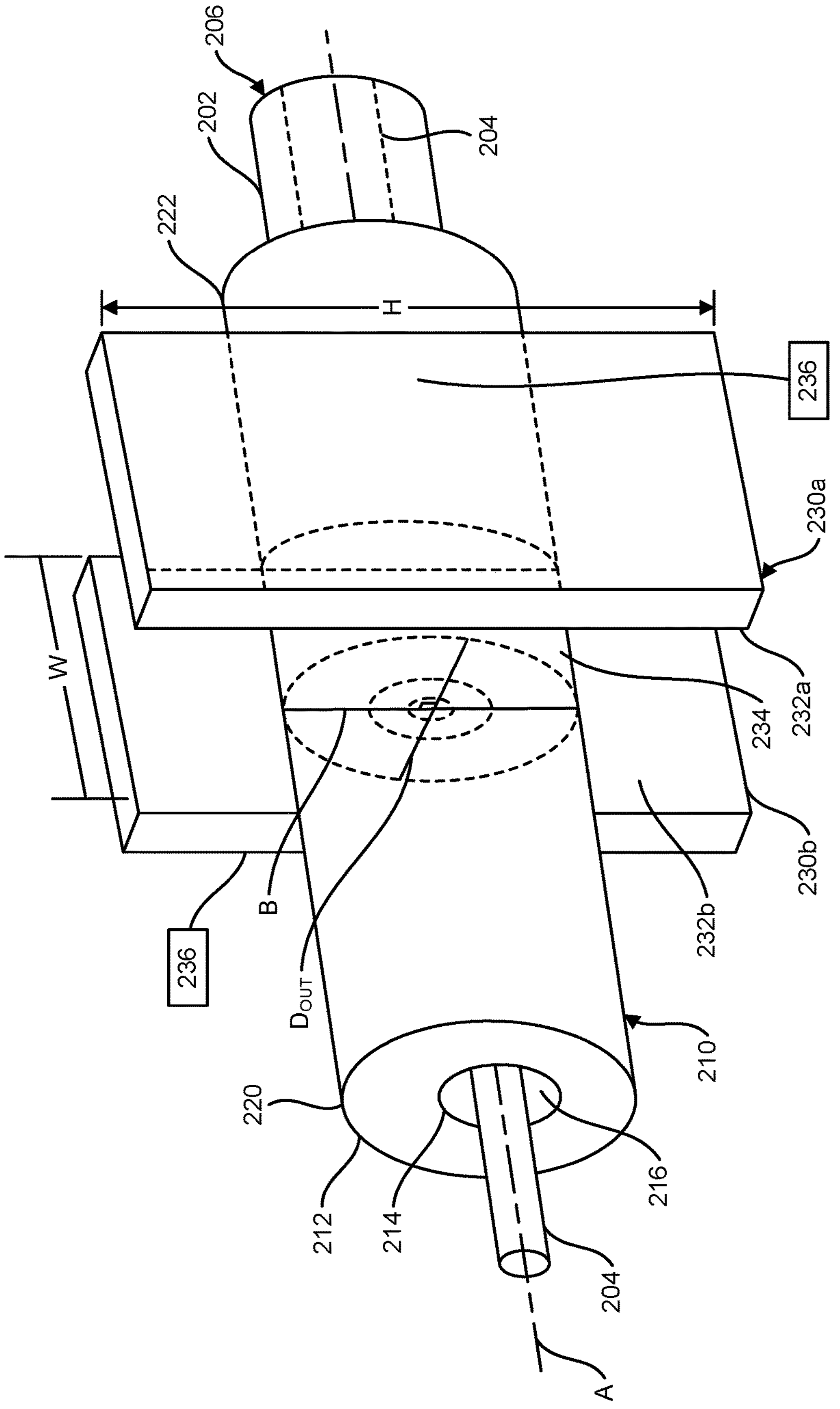
FIG. 2 is a schematic diagram illustrating an example catheter assembly lock mechanism for use with the example electrophysiology system of FIG. 1.

FIG. 2 illustrates a catheter assembly lock mechanism 200 that can be used with the example electrophysiology system 50 and can correspond with lock mechanism 120 of the example electroporation catheter system 60, which can be used with introducer sheath 110. In the example, the lock mechanism 200 is configured to be operably coupled to an elongated sheath 202 and configured to receive an elongated catheter 204 coaxially within the elongated sheath 202 to form a catheter assembly 206. The locking mechanism 200 includes a deformable tube 210 and a plurality of opposing paddles 230*a*, 230*b*. The deformable tube 210 includes an outer wall 212 and an inner wall 214. The inner wall 214 forms an axial lumen 216 along axis A. For illustration, the outer wall 212 includes a line segment of a secant passing through the axis A defined as an outer diameter $D_{out}$.

In the illustrated example, the deformable tube 210 includes an open, proximal end 220 and an open, distal end 222. The distal end 222 is configured to be operably coupled to the elongated sheath 202 having a sheath lumen along the axis A. The proximal end 220 is configured to receive a catheter 204 along axis A into lumen 216 and into the sheath lumen of sheath 202 to form the catheter assembly 206.

The plurality of at least partially overlapping opposing paddles 230*a*, 230*b*, which includes two paddles in the illustrated example, are disposed against the outer wall 212 of the deformable tube 210. Each of the paddles 230*a*, 230*b* includes a generally planar lock region 232*a*, 232*b* configured to interface with the outer wall 212 generally perpendicular to a secant line of the outer diameter $D_{out}$ such that the generally planar lock regions 232*a*, 232*b* are tangential to the outer wall 212 when in contact with the outer wall 212 at a point in its nominal, or undeformed, state. For example, the plane of the lock regions 232*a*, 232*b* are perpendicular to the secant line of the outer diameter $D_{out}$. In the illustrated example, the generally planar lock regions 232*a*, 232*b* are generally parallel to each other. The plurality of paddles 230*a*, 230*b* are movable with respect to each other. In one example, at least one of the paddles 230*a*, 230*b* is movable with respect to the deformable tube 210. In one example, the paddles 230*a*, 230*b* are movable with respect to the deformable tube 210 along a line of travel generally perpendicular to the axis A. In another example, the paddles 230*a*, 230*b* are movable with respect to the deformable tube 210 such that the planes of the lock regions 232*a*, 232*b* travel generally parallel to each other perpendicularly along the secant line of the outer diameter $D_{out}$. In the illustration, the generally planar lock regions 232*a*, 232*b* of the opposing paddles 230*a*, 230*b* overlap the deformable tube 210 when in contact with the outer wall 212 in an overlap region 234. The lock regions 232*a*, 232*b* include a height H and width W. In one example, the height of each lock region 232*a*, 232*b* is the same, and the width of each lock region 232*a*, 323*b* is the same.

A drive mechanism 236 can be employed to move and selectively position the paddles 230*a*, 230*b* with respect to the deformable tube 210. Several suitable drive mechanisms 234 are contemplated including hand positioning of the paddles 230*a*, 230*b* with respect to the deformable tube 210. For instance, the drive mechanism 236 can cause a selective movement of the paddles 230*a*, 230*b* may be electrically or mechanically actuated such as along rails, as pistons, as a rack and pinion, or other suitable instrument to maintain the line of travel perpendicular to the axis or along the secant line of the outer diameter $D_{out}$. In one example, the position of the paddles 230*a*, 230*b* with respect to the deformable tube 210, or the position of the lock regions 232*a*, 232*b* along the secant line of the outer diameter $D_{out}$ can be held in place by a suitable stopping mechanism used in connection with the drive mechanism 236. The drive mechanism 234 can be configured to move both paddles 230*a*, 230*b* toward the axis A and with respect to the deformable tube 210 at the same time or both paddles 230*a*, 230*b* away from the axis A with respect to the deformable tube 210 at the same time. In another example, the drive mechanism 236 can be configured to move one paddle toward the axis A and with respect to the deformable tube 210 and the other paddle or to move one paddle away from the axis A and with respect to the deformable tube 210 and the other paddle.

Figure 3A:
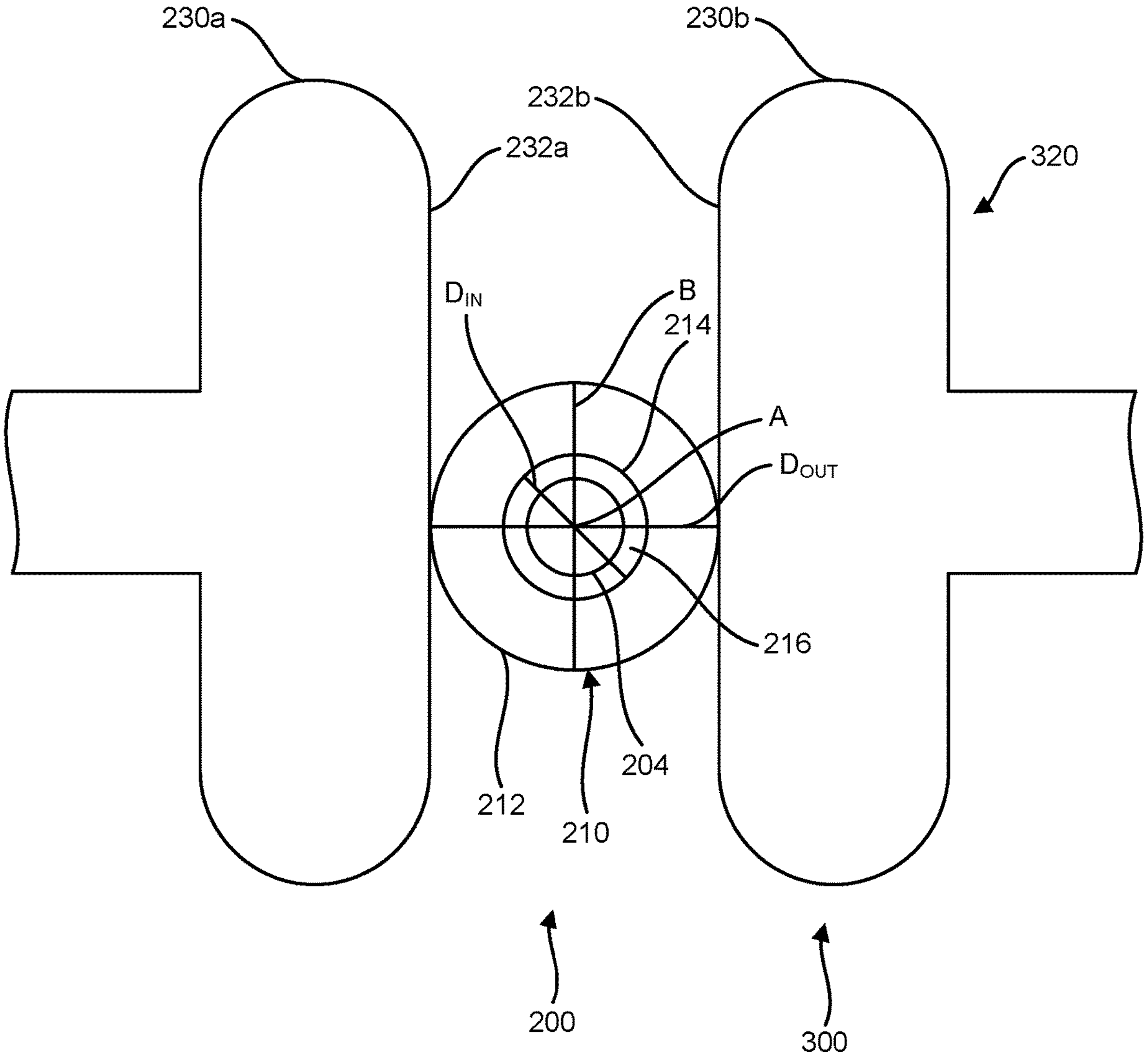
FIGS. 3A-3C are schematic diagrams of various example states of an example cross section of the example catheter assembly lock mechanism of FIG. 2.
Figure 3B:
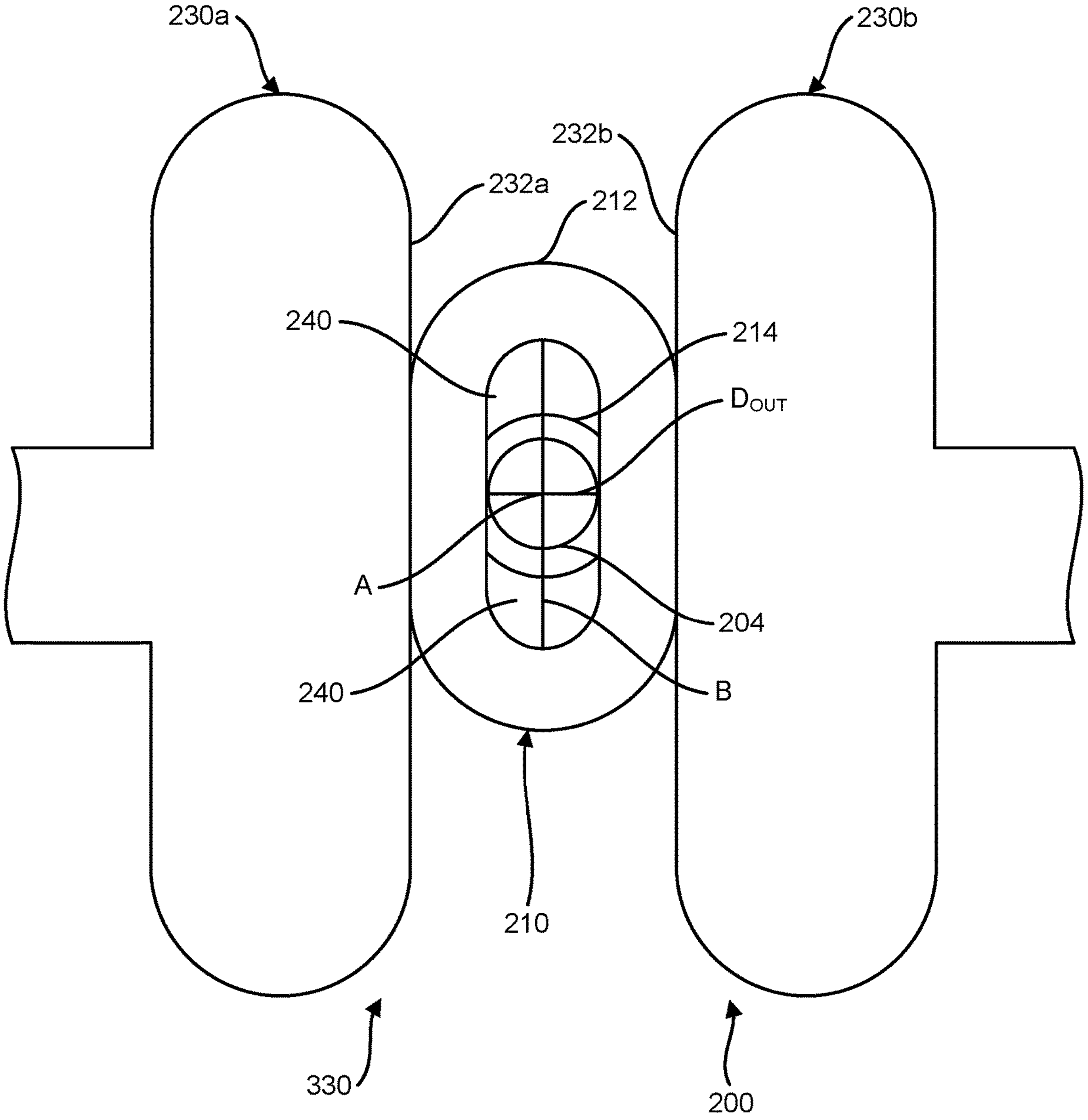
Figure 3C:
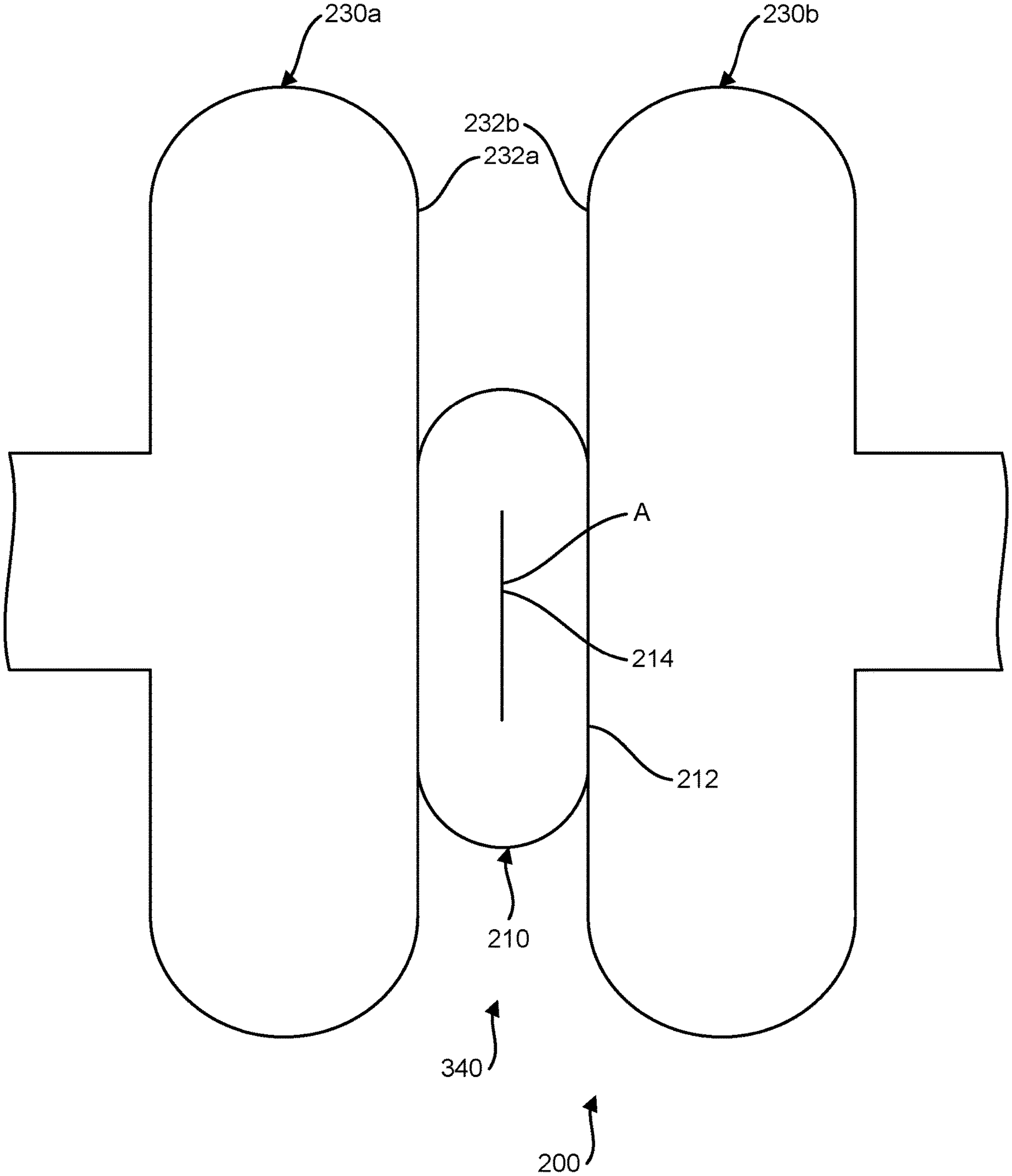

FIGS. 3A-3C illustrate various example states of a cross section 300 of the example catheter assembly lock mechanism 200 taken along lines 3-3 of FIG. 2, or in a cross-sectional plane perpendicular to the axis A. As illustrated, the paddles 230*a*, 230*b* are selectively positionable with respect to the deformable tube 210 to put the lock mechanism in one of a plurality of states based on a compression of the deformable tube as effected by the paddles 230*a*, 230*b*, which deforms the lumen 216. For illustration, a bisector line B passes through the axis A and perpendicular to the outer diameter $D_{out}$. The axis A and outer diameter $D_{out}$ lie in a diameter plane, and the axis A and bisector line B line in a bisector plane, which is perpendicular to the diameter plane. Also, the inner wall 214 includes a line segment of a secant passing through the axis A defined as an inner diameter $D_{in}$. The catheter 204 received in the lock mechanism 200 is selected to have a length of an outer diameter of the catheter is less than a length of the inner diameter $D_{in}$.

In a first state, or nominal state 320, as illustrated in FIG. 3A, the paddles 230*a*, 230*b* are not touching the outer wall 212 of the deformable tube 210 or lightly touching the outer wall 212. A catheter 204 is received in the lock mechanism 200. The length of the outer diameter of the catheter 204 is less than the length of the inner diameter $D_{in}$, and the catheter 204 can freely travel along the axis A with respect to the sheath 202. In the nominal state, the paddles 230*a*, 230*b* do not compress the inner wall 214 and do not deform the lumen 216, or do not compress the inner wall 214 or deform the lumen 216 enough, to pinch or apply a force against the catheter 204, which allows the catheter 204 to travel along the axis A with respect to the lock mechanism 200 and sheath 202. Additionally, the fluid, such as saline, can flow between the inner wall 214 and the catheter 204 and down the catheter assembly 206 such as in the lumen of the sheath 202 between the catheter 204 and sheath 202 in the nominal state 320.

In a second state, first compressed state, or sheath-lock state 330, as illustrated in FIG. 3B, the catheter 204 is received in the lock mechanism 200. The paddles 230*a*, 230*b* are releasably urged against the deformable tube 210 at the outer wall 212 to deform the inner wall 214, which pinches or applies a force along the line of the outer diameter $D_{out}$ against the catheter 204 in the overlap region 234 to hold the catheter 204 in place with respect to the deformable tube 210 and sheath 202. In the sheath-lock state 330, the paddles 230*a*, 230*b* compress the inner wall 214 and deform the lumen 216. In one example, the shape of the lumen 216 formed by the inner wall 214 in the cross-sectional plane perpendicular to the axis A of the overlap region 234 is no longer circular and has become ovalized. The distance of the cross-sectional shape of the lumen 216 formed by the inner wall 214 along the line of the outer diameter $D_{out}$ becomes the same as the length of the diameter C of the catheter 204. The distance of the cross-sectional shape of the lumen 216 formed by the inner wall 214 along the bisector line B becomes longer than the length of the diameter C of the catheter 204. In one example, the distance of the cross-sectional shape of the lumen 216 formed by the inner wall 214 along the bisector line B becomes longer than the length of the diameter of the lumen 216 in the nominal state. The collapsed deformable tube 210 pinching the catheter 204 in the overlap region 234 along the bisector plane includes openings 240 between the catheter 204 and the inner wall 214 along the bisector plane as illustrated along the bisector line B.

In the sheath lock state 330, the catheter 204 pinched in the lock mechanism 200 is not movable with respect to the sheath 202, but fluid, such as saline, can still flow through the lock mechanism 200 and down the catheter assembly 206.

In a third state, second compressed state, or air lock state 340, as illustrated in FIG. 3C, the catheter 204 is removed from the lock mechanism 200. The paddles 230*a*, 230*b* are releasably urged against the deformable tube 210 at the outer wall 212 to deform the inner wall 214 such as to collapse the deformable tube 210 and seal the lumen 216. The inner wall 214 is compressed together in the overlap region 234 along the diameter plane and the bisector plane as illustrated along the bisector line B. In the air lock state 340, fluid, such as saline or air, does not enter the sheath 202 from the proximal end 220. In the illustrated example, the height H of the lock regions is longer than the length of the diameter of the outer wall 212. For example, the height H is longer than one-half of the length of a circumference of an inner wall 214. For instance, at least one quarter of length of the circumference of the inner wall 214 is on each side of the diameter plane. In this configuration, the lock regions 232*a*, 232*b* can apply a force to the deformable tube 210 to the entire inner wall 214 along the overlap region 234 in the air lock state 340. Additionally, the width W is effectively at an amount to maintain the seal under the pressures applied within the lock mechanism 200.

FIGS. 4 and 5 illustrate a catheter lock mechanism 400 that can be used with the example electrophysiology system 50 and can correspond with lock mechanism 120 of the example electroporation catheter system 60 and with example lock mechanism 200. In the example, the lock mechanism 400 is configured to be operably coupled to an elongated sheath 402 and configured to receive an elongated catheter 404 coaxially within the elongated sheath 402 to form a catheter assembly 406. The locking mechanism 400 includes a deformable tube 410 and a plurality of opposing paddles 430*a*, 430*b*. The deformable tube 410 includes an outer wall 412. The deformable tube 410 includes a proximal end 420 and a distal end 422. The lock mechanism 400 includes a proximal hub 424 coupled to the proximal end 420 of the deformable tube 410 to receive the catheter 404. The lock mechanism 400 also includes a distal hub 426 coupled to the distal end 422 of the deformable tube 410 coupled to the sheath 402. In the example, the proximal hub 424 is a valve hub which can be coupled to a tubing to receive a fluid such as saline into the lock mechanism 400. The valve hub can also create a dynamic seal on the catheter 404 to reduce the likelihood of air ingress or fluid leaks during use even if the catheter is moved or translated. The proximal hub 424 can be configured in shape to receive and guide the catheter 404 along an axis AA of the lock mechanism 400 and the catheter assembly 406. The distal hub 426 is configured to be operably coupled to the elongated sheath 402 so as to hold the sheath 402 in place with respect to the lock mechanism 400.

The plurality of at least partially overlapping opposing paddles 430*a*, 430*b*, which includes two paddles in the illustrated example, are disposed against the outer wall 412 of the deformable tube 410. Each of the paddles 430*a*, 430*b* includes a generally planar lock region 432*a*, 432*b* generally parallel to each other. The lock regions 432*a*, 432*b* are configured to interface with the outer wall 412 generally in an overlap region 434. The generally planar lock regions 432*a*, 432*b* are tangential to the outer wall 412 when in contact with the outer wall 412 at a point in its nominal, or undeformed, state. The plurality of paddles 430*a*, 430*b* are movable with respect to each other and with the deformable tube 410, such as via a drive mechanism (not shown). In one example, the paddles 430*a*, 430*b* are coupled to a shaft 436*a*, 436, and the shafts 436*a*, 436*b* can be coupled to the drive mechanism.

The flexible tube 410 is selected from a material that is soft and resilient to flex through a number of locking and unlocking cycles without tearing or permanently deforming. Additionally, the thickness of the wall of the flexible tube is selected to compress under the force of the paddles 430*a*, 430*b*. Further, the length of the flexible tube is selected such that the portions deformed under force of the paddles do not overly stress the bonds at the ends 420, 422 with the hubs 424, 426. For example, the ends 420 and 422 are spaced-apart from the overlap region 434.

Figure 4A:
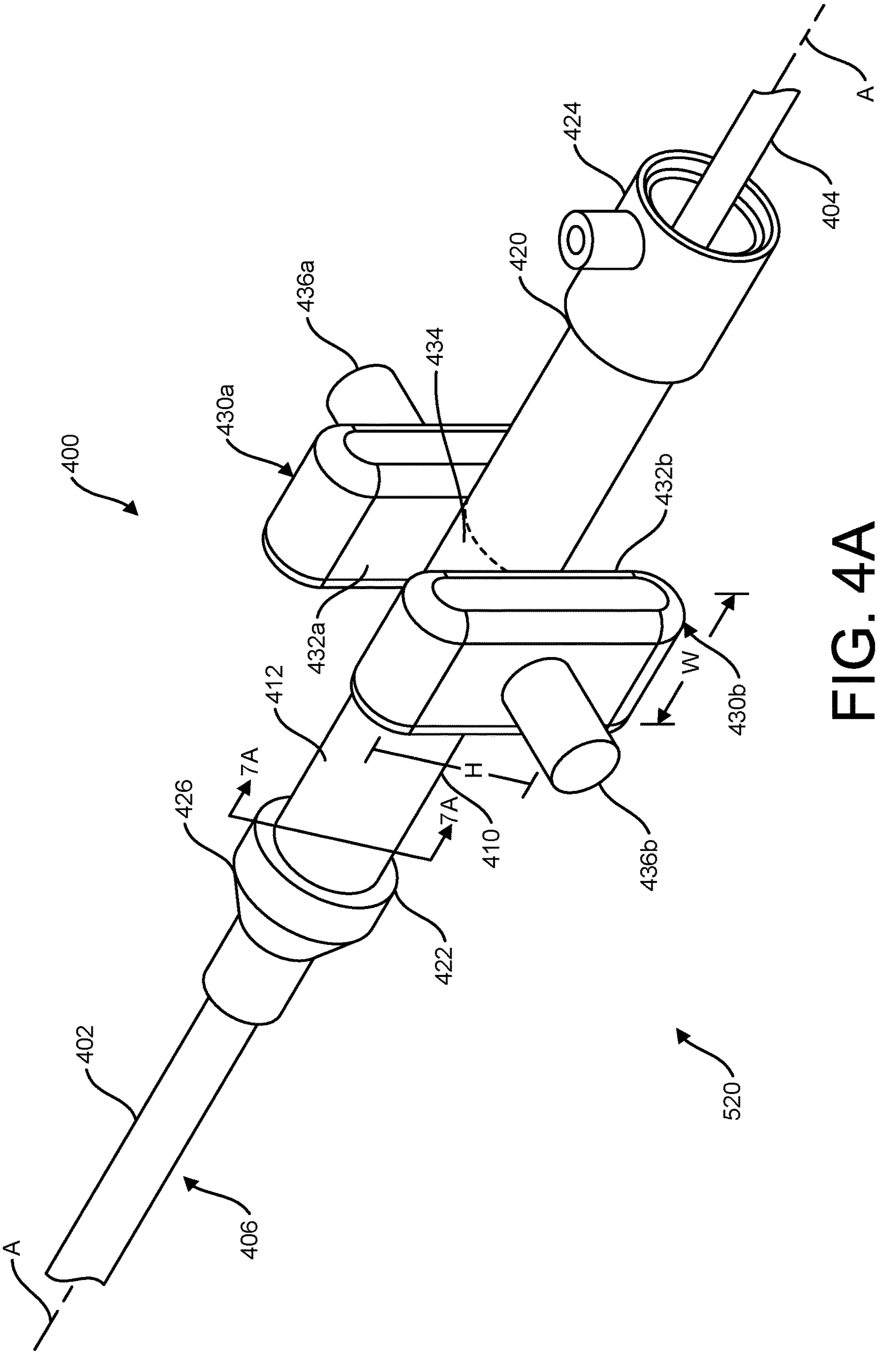
FIGS. 4A-4C are perspective views of an example catheter assembly lock mechanism for use with the example electrophysiology system of FIG. 1 in the states of FIGS. 3A-3C.
Figure 5A:
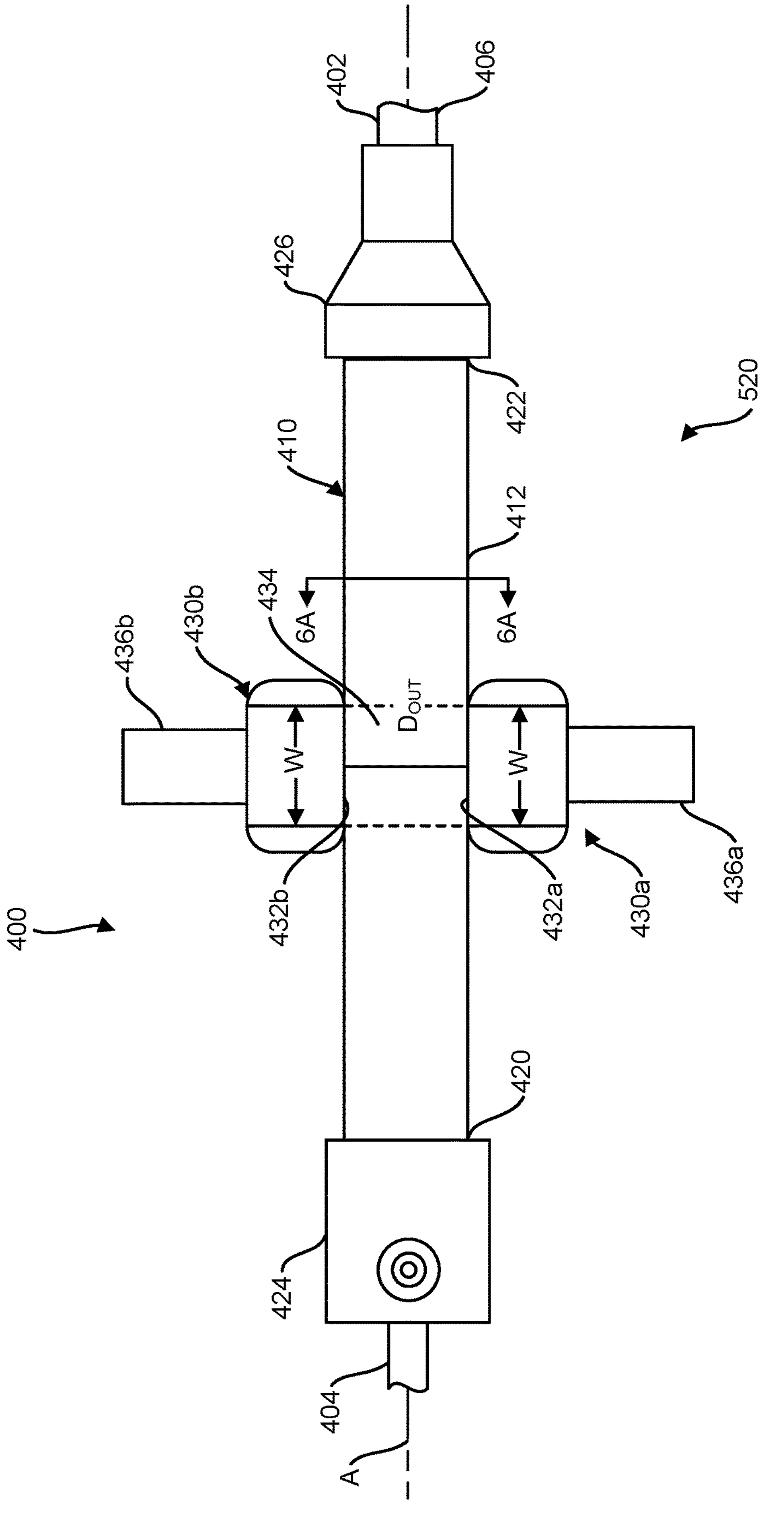
FIGS. 5A-5C are top views of the example catheter assembly lock mechanism in the states of FIGS. 4A-4C.

FIGS. 4A and 5A illustrate the lock mechanism 400 in the first state, or the nominal state 520. The paddles 430*a*, 430*b* are not touching the outer wall 412 of the deformable tube 410 or the lock regions 432*a*, 432*b* are lightly touching the outer wall 412 and the lock regions 432*a*, 432*b* are spaced apart by a first distance. A catheter 404 is received in the lock mechanism 400, and the catheter 404 can freely travel along the axis AA with respect to the lock mechanism 400 and the sheath 402. In the nominal state, a fluid, such as saline, can flow into the lock mechanism 400 and down the catheter assembly 206 such as in the lumen of the sheath 202 between the catheter 204 and sheath 202 in the nominal state 520.

Figure 4B:
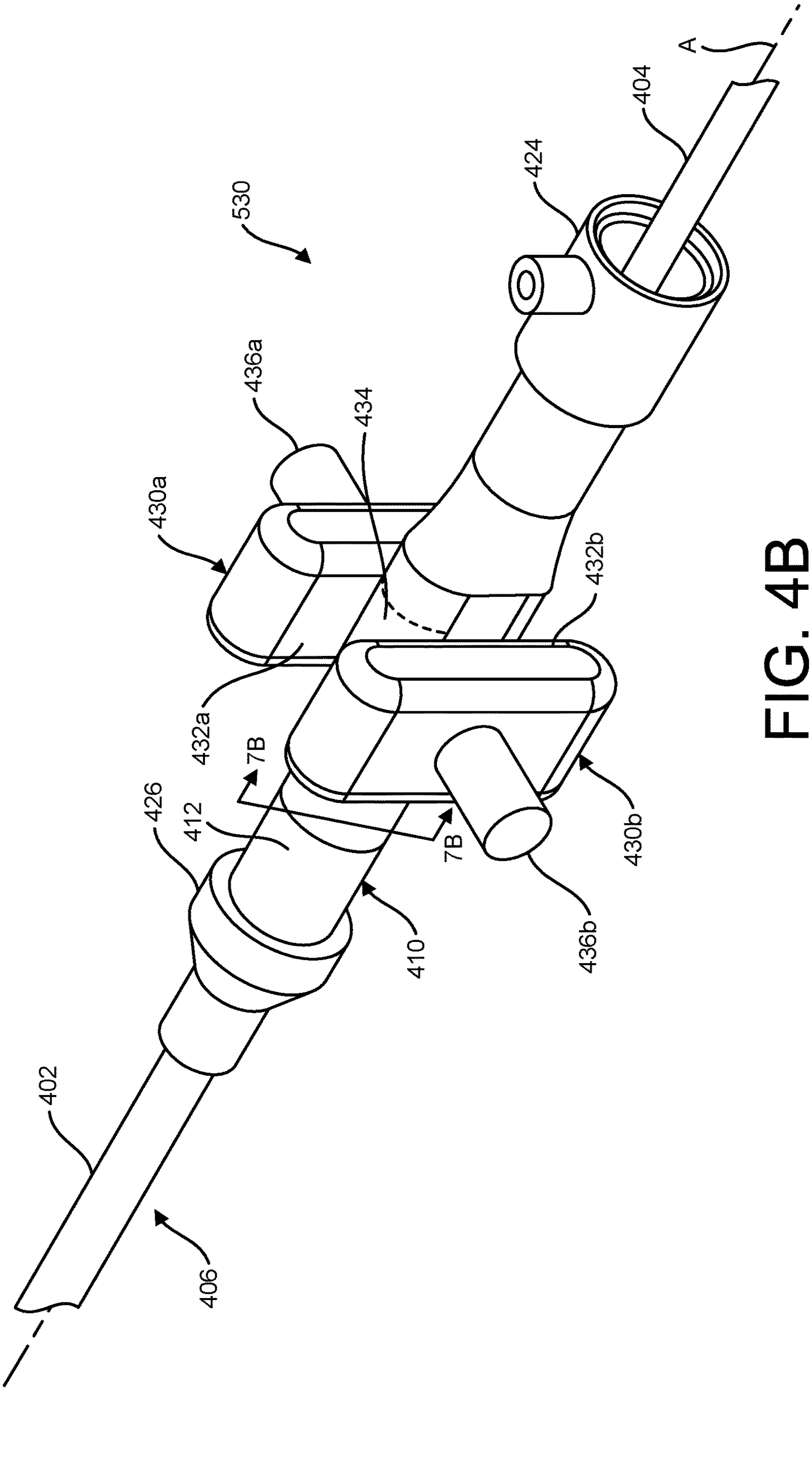
Figure 5B:
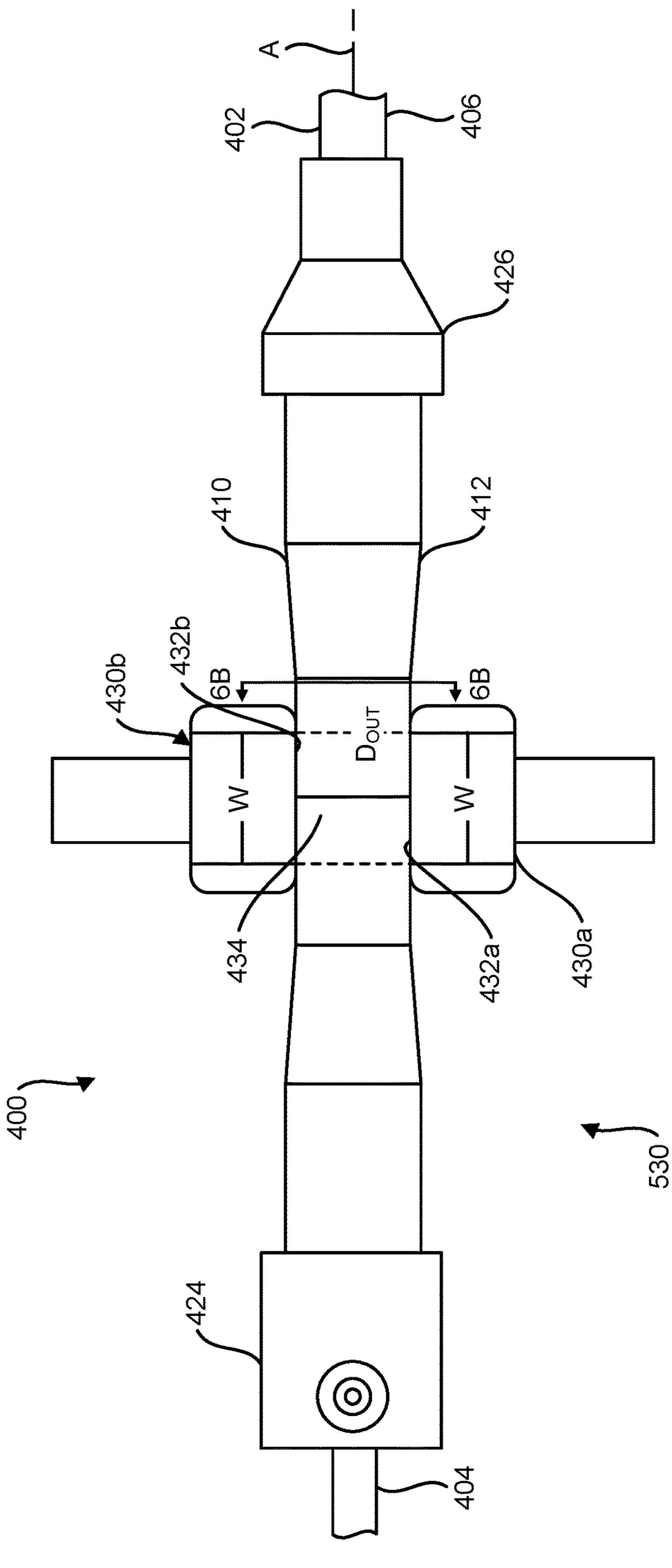

FIGS. 4B and 5B illustrate the lock mechanism 400 in the second state or sheath lock state 530. The catheter 404 is received within the lock mechanism 400 in the sheath lock state 530. The paddles 430*a*, 430*b* are releasably urged, such as with the drive mechanism, against the deformable tube 410 in the overlap region 434 to deform, or flatten, the tube 410. The lock regions 432*a*, 432*b* are spaced apart from each other by a second distance that is less than the first distance. The deformable tube is collapsed against the catheter 404, and the force of the paddles 430*a*, 430*b* in a direction toward the axis AA is at least enough to hold the catheter 404 in place with respect to the deformable tube 410 and the sheath 402. A clinician can select the sheath lock state 530 prior to performing an ablation, such as by electroporation, to lessen the likelihood that the catheter 404 will migrate via the shaft 402 and, in particular, that electrodes on the catheter shaft will migrate into the sheath 402.

Figure 4C:
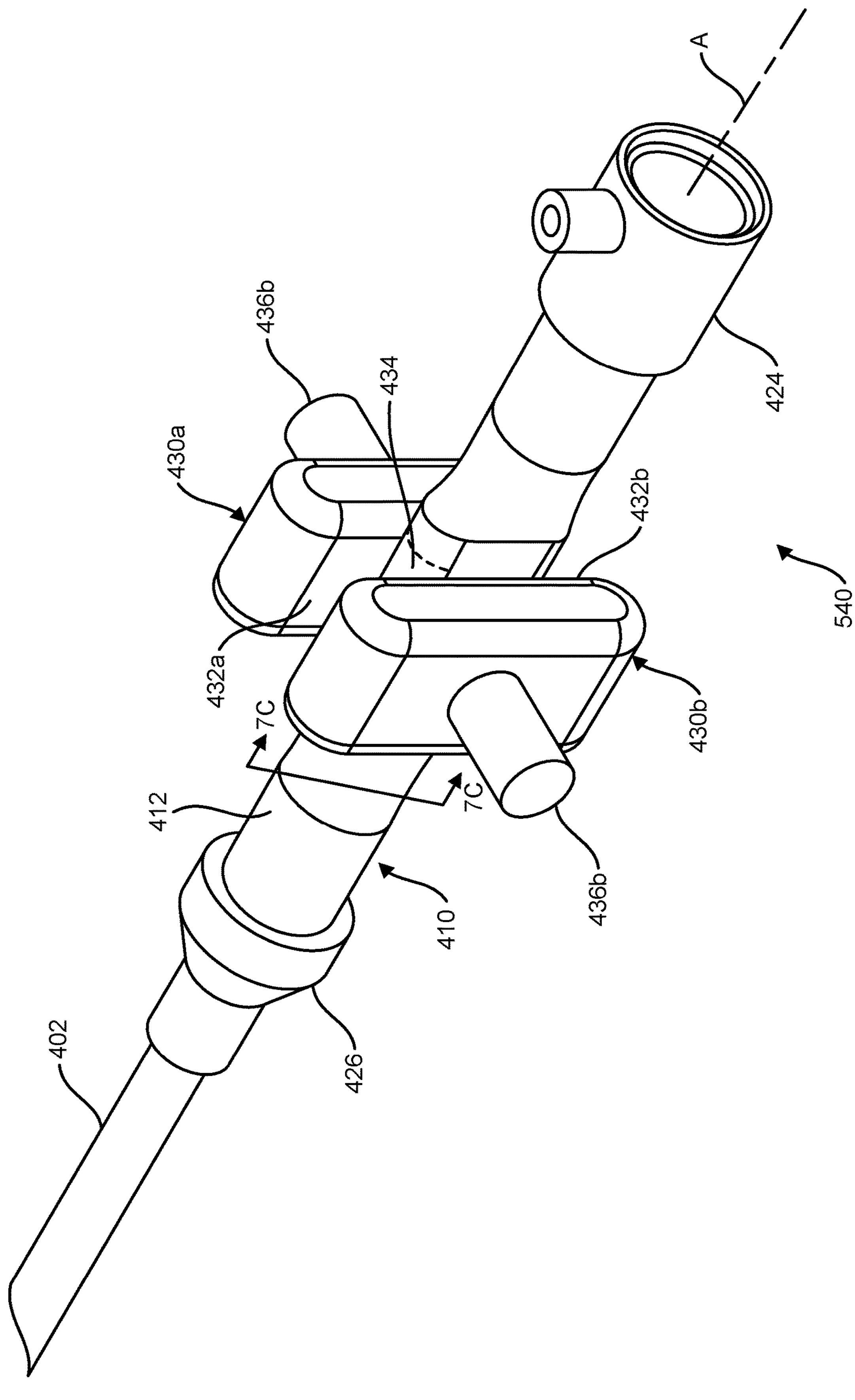
Figure 5C:
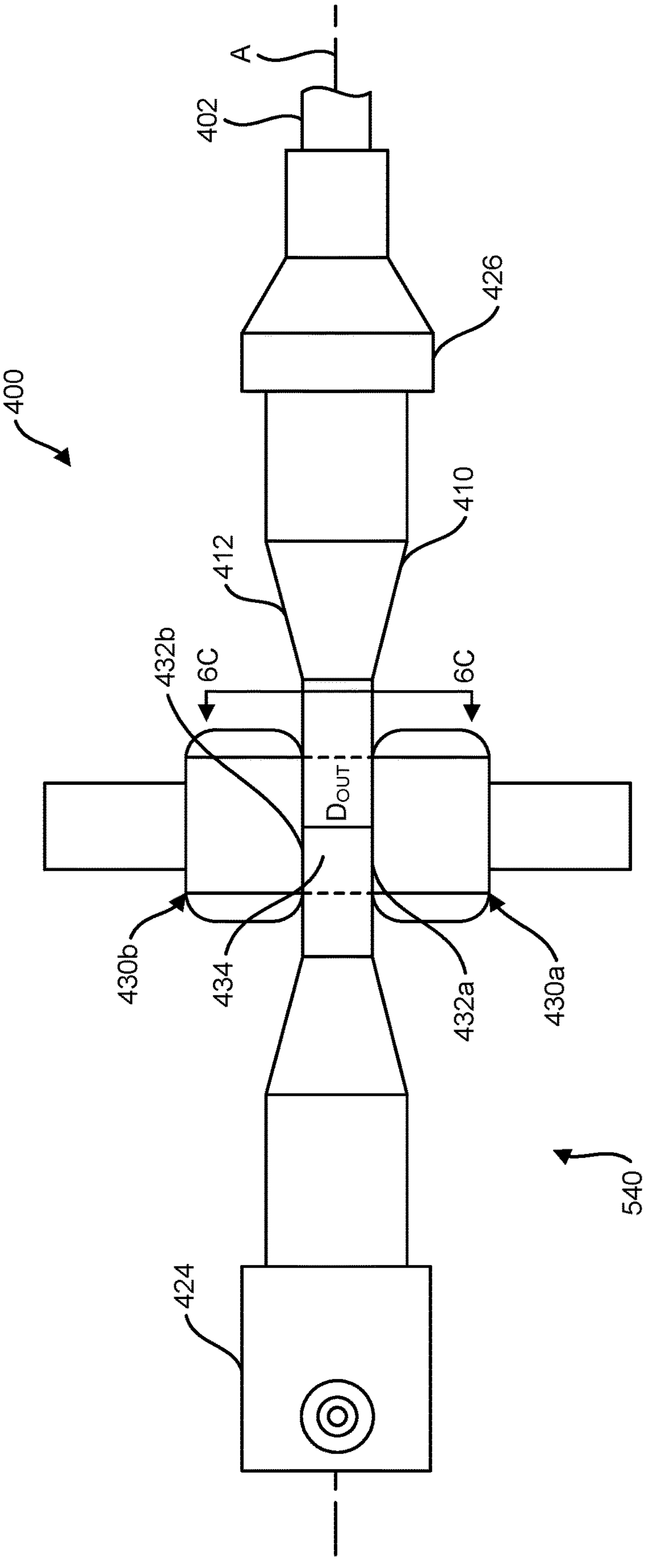

FIGS. 4C and 5C illustrate the lock mechanism 400 in the third state or an air lock state 540. The catheter 404 is removed from the lock mechanism 400 and is not present in the lock mechanism 400 in the sheath lock state 540. The paddles 430*a*, 430*b* are releasably urged, such as with the drive mechanism, against the deformable tube 410 in the overlap region 434 to deform, or flatten, the tube 410. The lock regions 432*a*, 432*b* are spaced apart from each other by a third distance that is less than the second distance. The deformable tube is collapsed, and the force of the paddles 430*a*, 430*b* in a direction toward the axis is at least enough to seal an inner lumen within the deformable tube. A clinician can select the air lock state 540 such as prior to device insertion into the sheath 402 to reduce the likelihood of air ingress into the sheath 402. The paddles 430*a*, 430*b* can be configured to provide a constant positive pressure against the deformable tube 410 via the drive mechanism while in the sheath lock state 430 and air lock state 440.

Figure 6A:
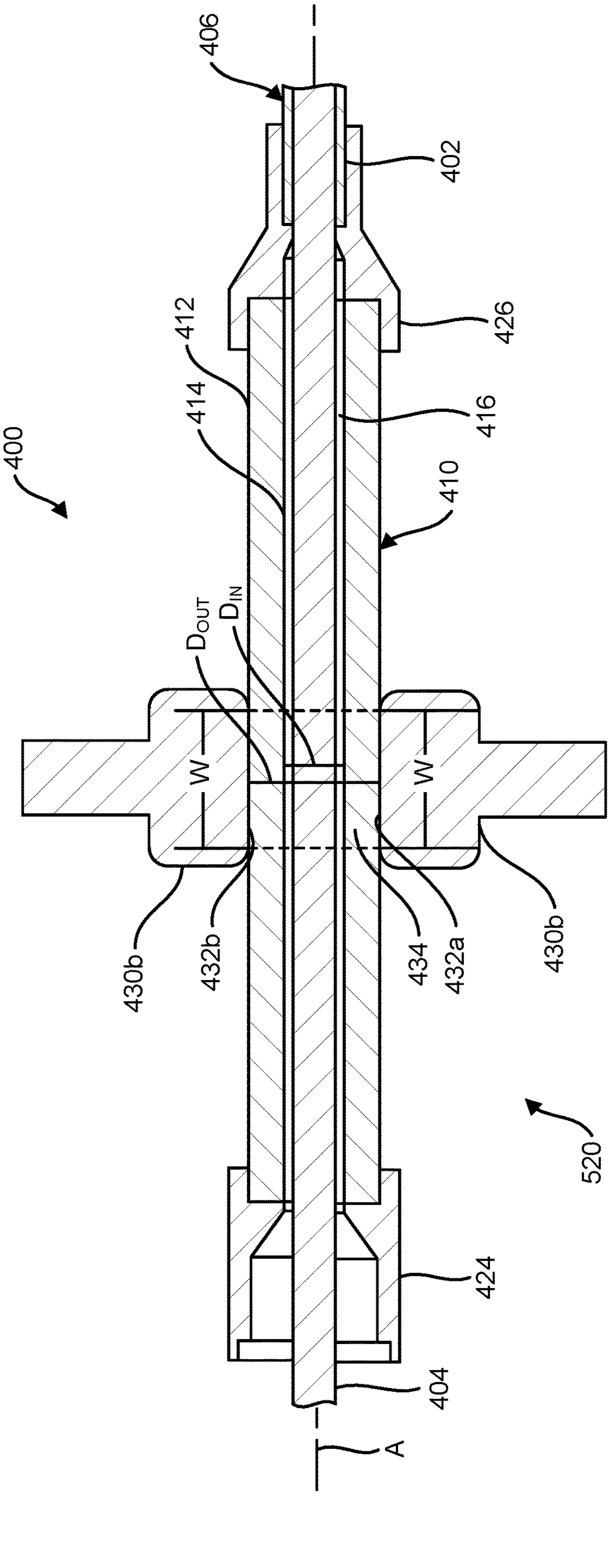
FIGS. 6A-6C are sectioned top views of the example catheter assembly lock mechanism in the states of FIGS. 5A-5C.
Figure 6B:
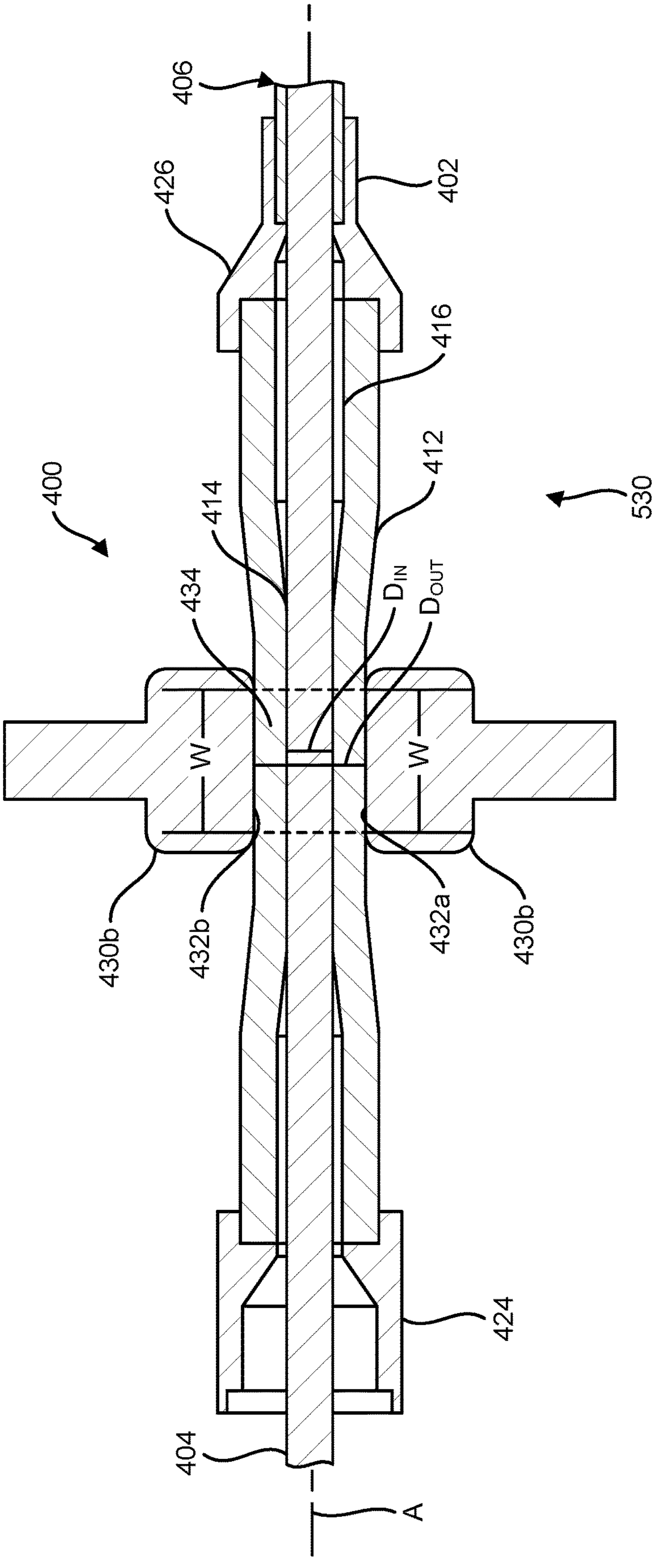
Figure 6C:
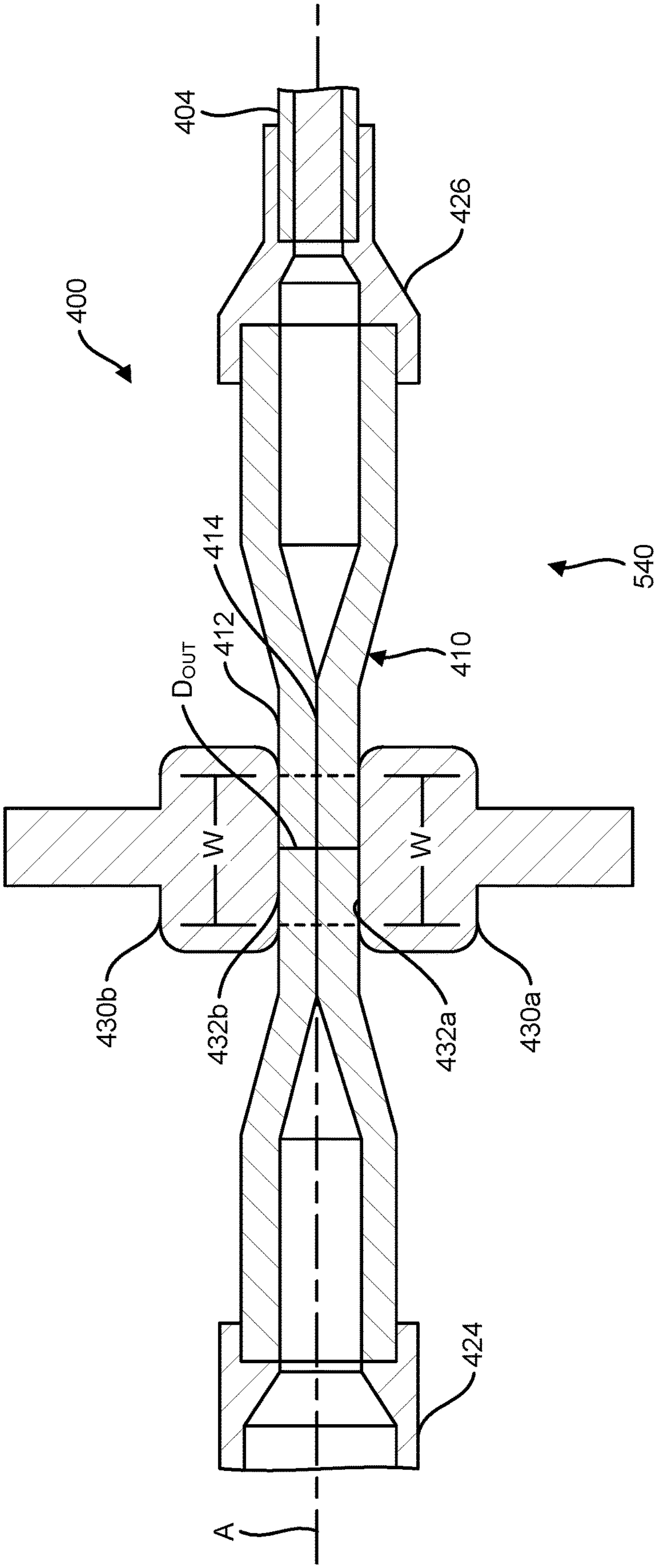

FIGS. 6A-6C illustrate a cross section 600 of the lock mechanism 400 taken along lines 6-6 of FIGS. 5A-5C in the various states of the lock mechanism 400, such as a top cross sectional view. For instance, the cross section can be taken along the diameter plane in FIGS. 3A-3C. FIGS. 6A-6C illustrate the proximal hub 424 configured to guide the catheter 404 into an inner lumen 416 of the deformable tube 410 formed by an inner wall 414 of the deformable tube 410. The distal hub 426 is configured to attach to the sheath 402 and hold the sheath 404 in place with respect to the lock mechanism 400. As the view of the lock mechanism 400 in the diameter plane, the inner wall 414 includes a line segment of a secant passing through the axis AA defined as an inner diameter $D_{in}$, and the outer wall 412 includes a line segment of a secant passing through the axis A defined as an outer diameter $D_{out}$.

The generally planar lock regions 432*a*, 432*b* are tangential to the outer wall 412 when in contact with the outer wall 212 at a point in its nominal, or undeformed, state in FIG. 6A, taken along lines 6A-6A of FIG. 5A. Also, the plane of the lock regions 432*a*, 432*b* are perpendicular to the secant line of the outer diameter $D_{out}$ in FIGS. 6A-6C. In the illustrated example, the generally planar lock regions 432*a*, 432*b* are generally parallel to each other. The plurality of paddles 430*a*, 430*b* are movable with respect to each other. In one example, the paddles 430*a*, 430*b* are movable with respect to the deformable tube 410 along a line of travel generally perpendicular to the axis AA. In another example, the paddles 430*a*, 430*b* are movable with respect to the deformable tube 410 such that the planes of the lock regions 432*a*, 432*b* travel generally parallel to each other perpendicularly along the secant line of the outer diameter $D_{out}$. In the illustration, the generally planar lock regions 432*a*, 432*b* of the opposing paddles 430*a*, 430*b* overlap the deformable tube 410 when in contact with the outer wall 412 in an overlap region 434. The lock regions 432*a*, 432*b* includes a width W to provide an overlap region 434 that is long enough on the axis AA to maintain hold of the catheter in the sheath lock state 530 of FIG. 6C and to maintain a seal of the inner wall 414 under the positive pressure within the lock mechanism 400 in the air lock state 540 of FIG. 6C. In one example, the paddles 430*a*, 440*b* are positioned such that the width of each lock region 432*a*, 432*b* are in the overlap region 434.

In the first state, or nominal state 520, as illustrated in FIG. 6A, the paddles 430*a*, 430*b* lightly touch the outer wall 412. The length of the outer diameter of the catheter 404 is less than the length of the inner diameter $D_{in}$, and the catheter 404 can freely travel along the axis A with respect to the inner wall 414 and the sheath 402.

In the second state, or sheath-lock state 530, as illustrated in FIG. 6B, taken along lines 6B-6B of FIG. 5B, the catheter 404 is received in the lock mechanism 400. The paddles 430*a*, 430*b* are releasably urged against the deformable tube 410 at the outer wall 412 to deform the inner wall 414, which pinches or applies a force along the line of the outer diameter $D_{out}$ against the catheter 404 in the overlap region 434 to hold the catheter 404 in place with respect to the deformable tube 410 and sheath 402. In the sheath-lock state 530, the paddles 430*a*, 430*b* compress the inner wall 414 and deform the lumen 416.

In the third state, or air lock state 540, as illustrated in FIG. 6C, taken along lines 6C-6C of FIG. 5C, the catheter 504 is removed from the lock mechanism 500. The paddles are releasably urged against the deformable tube 510 at the outer wall 512 to deform the inner wall 514 such as to collapse the deformable tube 510 and seal the lumen 516 in the diameter plane. The inner wall 414 is compressed together in the overlap region 434 so that fluid, such as saline or air, does not enter the sheath 402 from the lock mechanism 400.

Figure 7A:
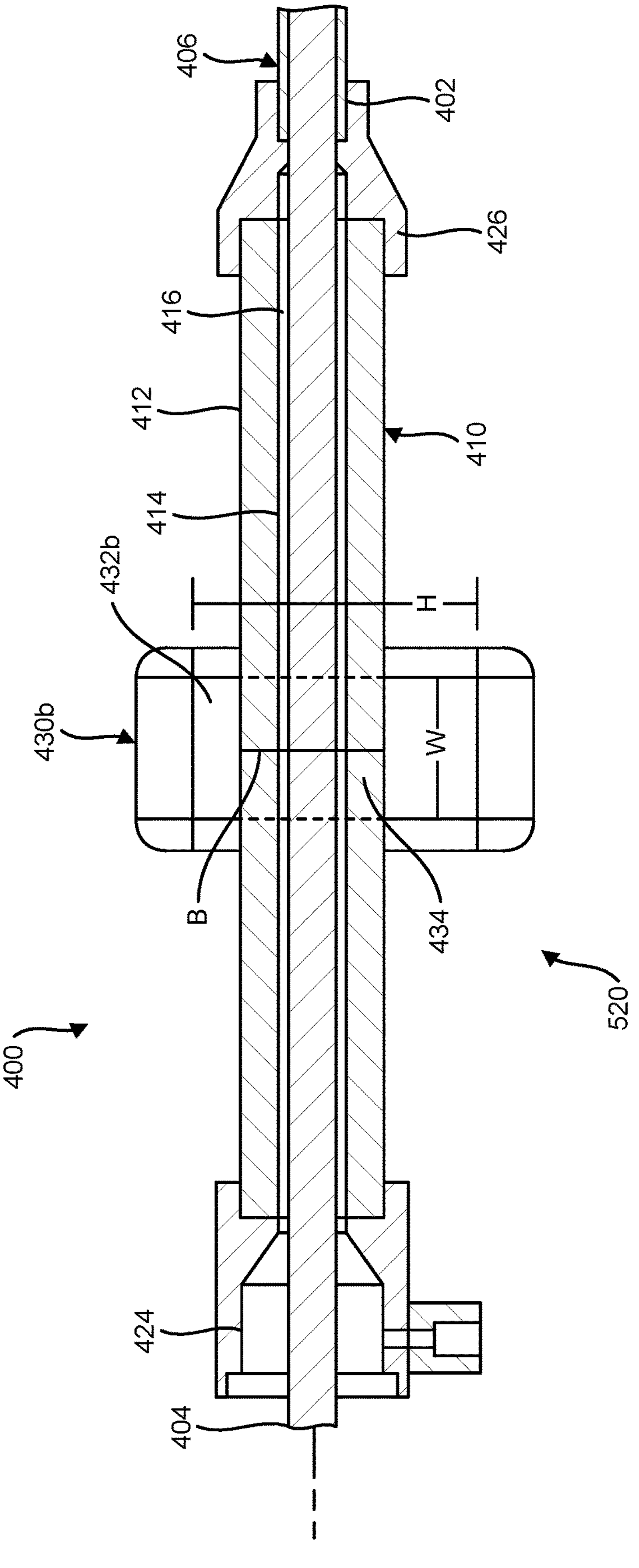
FIGS. 7A-7C are sectioned side views of the example catheter assembly lock mechanism in the states of FIGS. 4A-4C.
Figure 7B:
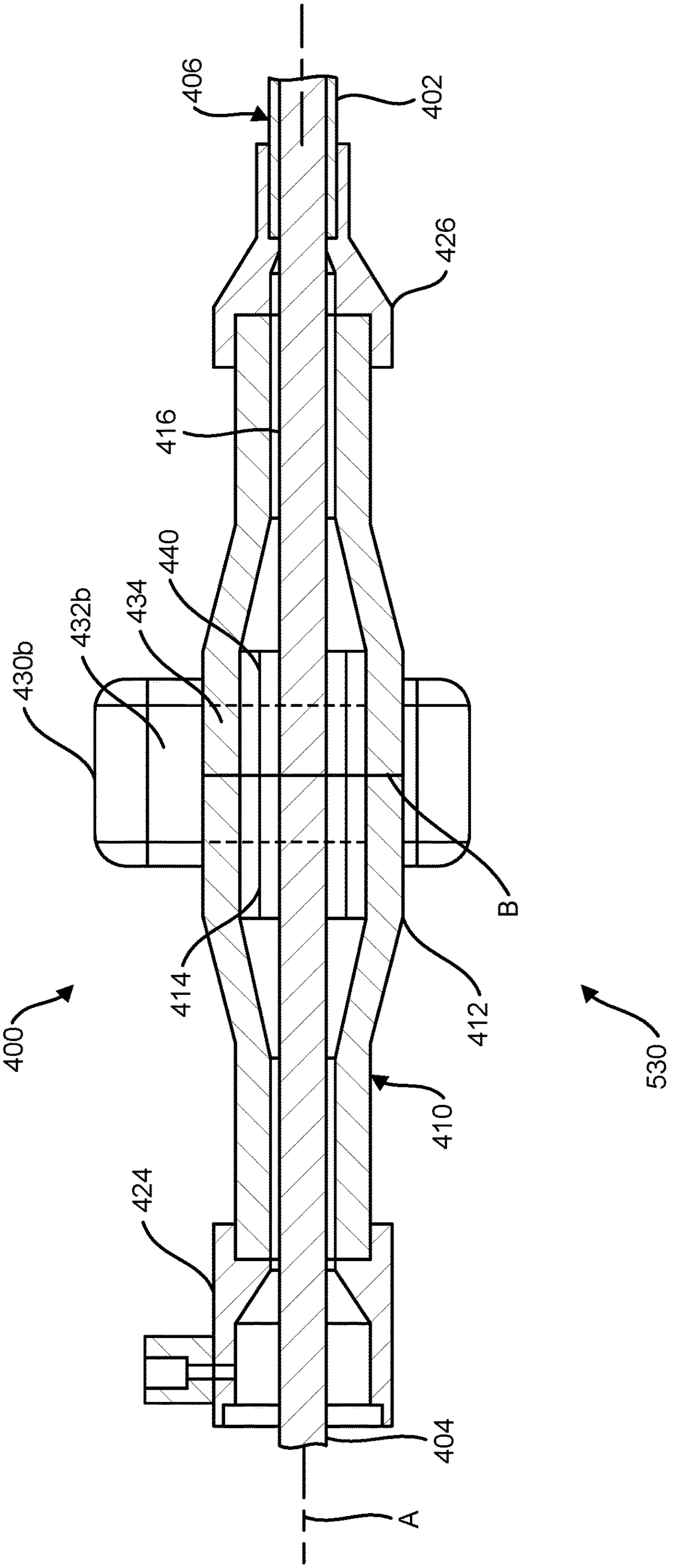
Figure 7C:
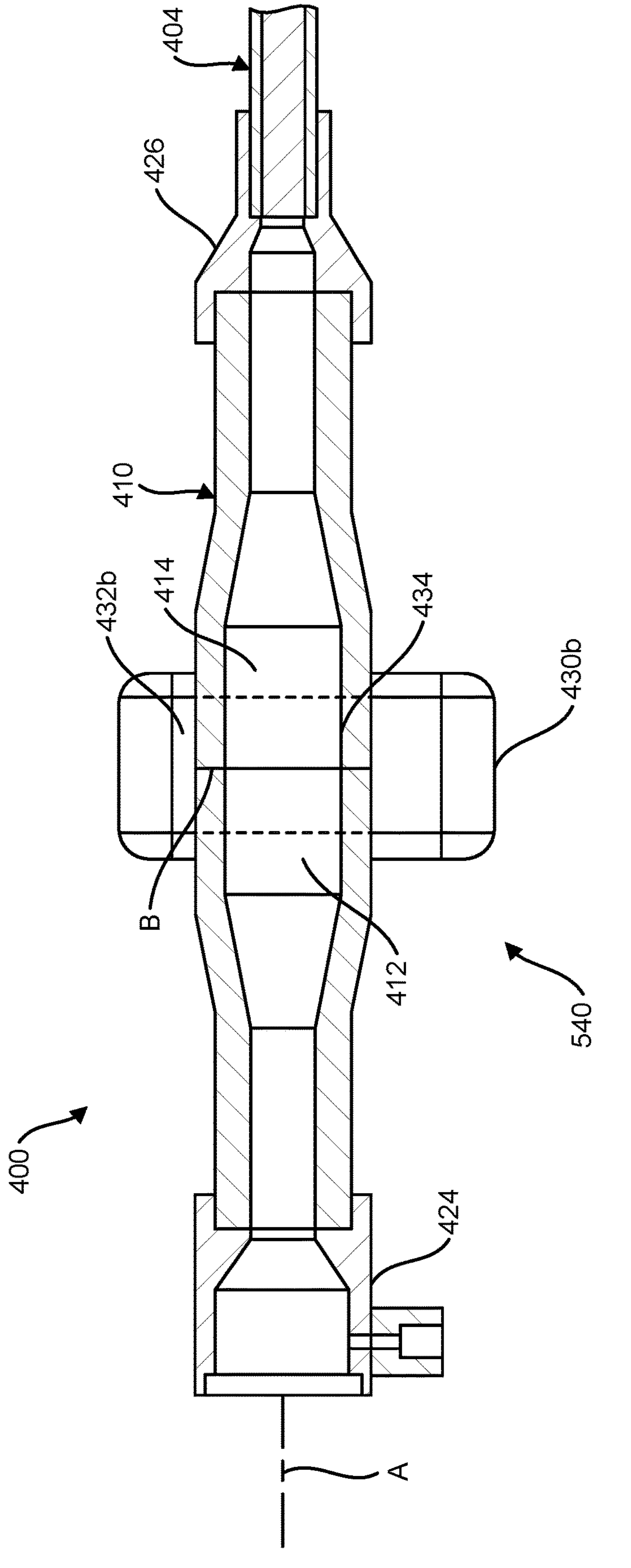

FIGS. 7A-7C illustrate a cross section 700 of the lock mechanism 400 taken along lines 7-7 of FIGS. 4A-4C in the various states of the lock mechanism 400, such as a side cross sectional view. For instance, the cross section can be taken along the bisector plane in FIGS. 3A-3C. As the view of the lock mechanism 400 in the bisector plane, the outer wall 412 includes a line segment of a secant passing through the axis AA defined as the bisector line B.

In the first state, or nominal state 520, as illustrated in FIG. 7A, taken along lines 7A-7A of FIG. 4A, the catheter 404 is received in the lock mechanism 400. The paddles 430*a*, 430*b* do not contact the deformable tube in a way to deform the inner wall 414 enough to prevent the catheter 404 from moving freely along axis AA. In particular, the inner wall 414 is not deformed along the bisector line B to prevent the catheter 404 from freely moving along axis AA.

In the second state, or sheath lock state 530, as illustrated in FIG. 7B, taken along lines 7B-7B of FIG. 4B, the paddles 430*a*, 430*b* are releasably urged against the deformable tube 410 at the outer wall 412 to deform the inner wall 414, which pinches or applies a force along the line of the outer diameter $D_{out}$ against the catheter 404 in the overlap region 434 to hold the catheter 404 in place with respect to the deformable tube 410 and sheath 402. The paddles 430*a*, 430*b* compress the inner wall 414 and deform the lumen 416. In one example, the shape of the lumen 416 formed by the inner wall 414 in the overlap region 434 is no longer circular and has become ovalized. The distance of the cross-sectional shape of the lumen 416 formed by the inner wall 414 along the bisector line B becomes longer than the length of the diameter C of the catheter 404. In one example, the distance of the cross-sectional shape of the lumen 416 formed by the inner wall 414 along the bisector line B becomes longer than the length of the diameter of the lumen 416 in the nominal state. The collapsed deformable tube 410, which is pinching the catheter 404, in the overlap region 434 along the bisector plane includes openings 440 between the catheter 404 and the inner wall 414 along the bisector plane as illustrated along the bisector line B. In the sheath lock state 530, the catheter 404 pinched in the lock mechanism 400 is not movable with respect to the sheath 402, but fluid, such as saline, can still flow through the lock mechanism 400 and down the catheter assembly 406. As illustrated in FIG. 7B, saline can flow down the catheter assembly 406 via openings 440 even though the catheter 404 is pinched against the inner wall 414 along the diameter plane, as illustrated in FIG. 6B.

In the third state, or air lock state 540, as illustrated in FIG. 7C, taken along lines 7C-7C of FIG. 4C, the catheter 404 is removed from the lock mechanism 400. The paddles 430*a*, 430*b* are releasably urged against the deformable tube 410 at the outer wall 412 to deform the inner wall 414 such as to collapse the deformable tube 410 and seal the lumen 416. The inner wall 414 is compressed together in the overlap region 434 along the diameter plane and the bisector plane as illustrated along the bisector line B. In the air lock state 540, fluid, such as saline or air, does not enter the sheath 402 from the proximal end 420. In the illustrated example, the height H of the lock regions is longer than the length of the diameter of the outer wall 412. In this configuration, the lock regions 432*a*, 432*b* can apply a force to the deformable tube 410 to the entire inner wall 414 along the overlap region 434 in the air lock state 440. Additionally, the width W is effectively at an amount to maintain the seal under the pressures applied within the lock mechanism 400.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A medical device for use with a catheter assembly including an elongated catheter coaxially disposed within a sheath, the medical device comprising:

a deformable tube having a proximal end, a distal end, an outer wall with an outer diameter, and an inner wall forming an axial lumen, the distal end configured to attach to the sheath, the proximal end configured to receive the catheter into the lumen; and a plurality of opposing paddles disposed against the outer wall, each of the opposing paddles having a generally planar lock region configured to be disposed against outer wall at the outer diameter, the lock surface disposed tangentially to the deformable tube, the plurality of opposing paddles laterally movable with respect to the deformable tube along the outer diameter;

the medical device having a first compressed state wherein the catheter is coaxially disposed within the sheath and the opposing paddles are releasably urged against the deformable tube at the outer diameter to collapse the deformable tube to hold the catheter in place with respect to the sheath and deformable tube, the collapsed deformable tube to form an elongated opening along the inner wall and the catheter; and the medical device having a second compressed state wherein the catheter is not coaxially disposed within the sheath and removed from the deformable tube and the opposing paddles are releasably urged against the deformable tube at the outer diameter to collapse the deformable tube and seal the lumen.

2. The medical device of claim 1, and further comprising a nominal state wherein the catheter is coaxially disposed within the sheath, and the catheter is movable with respect to the sheath and the deformable tube.

3. The medical device of claim 2, wherein the inner wall includes a circular cross section in the nominal state.

4. The medical device of claim 3, wherein the lock regions include a height and the inner wall includes a circumference, and wherein the height is at least half the circumference.

5. The medical device of claim 3, wherein the inner wall includes an ovalized cross section in the first compressed state.

6. The medical device of claim 1, wherein lock regions form an overlapping region on the deformable tube and the proximal end and distal end are spaced apart from the overlapping region.

7. The medical device of claim 1, and further comprising a drive mechanism operably coupled to the plurality of paddles, the drive mechanism configured to laterally move the plurality of opposing paddles with respect to the deformable tube.

8. The medical device of claim 1, wherein the proximal end includes a proximal hub configured to guide the catheter into the lumen, and the distal end includes a distal hub configured to attach to the sheath.

9. The medical device of claim 1, wherein the plurality of opposing paddles includes two opposing paddles, and wherein the lock regions are generally parallel to each other.

10. A medical system, comprising:

a catheter assembly having an elongated catheter coaxially disposable within a sheath; and a locking mechanism, comprising:

a deformable tube having a proximal end, a distal end, an outer wall with an outer diameter, and an inner wall forming an axial lumen, the distal end configured to attach to the sheath, the proximal end configured to receive the catheter into the lumen; and a plurality of opposing paddles disposed against the outer wall, each of the opposing paddles having a generally planar lock region configured to be disposed against outer wall at the outer diameter, the lock surface disposed tangentially to the deformable tube, the plurality of opposing paddles laterally movable with respect to the deformable tube along the outer diameter;

the medical system having a first compressed state wherein the catheter is coaxially disposed within the sheath and the opposing paddles are releasably urged against the deformable tube at the outer diameter to collapse the deformable tube to hold the catheter in place with respect to the sheath and deformable tube, the collapsed deformable tube to form an elongated opening along the inner wall and the catheter; and the medical system having a second compressed state wherein the catheter is not coaxially disposed within the sheath and removed from the deformable tube and the opposing paddles are releasably urged against the deformable tube at the outer diameter to collapse the deformable tube and seal the lumen.

11. The medical system of claim 10, wherein the catheter assembly is configured to perform an irreversible electroporation.

12. The medical system of claim 10, and further comprising a nominal state wherein the catheter is coaxially disposed within the sheath, and the catheter is movable with respect to the sheath and the deformable tube.

13. The medical system of claim 10, and further comprising a drive mechanism operably coupled to the plurality of paddles, the drive mechanism configured to laterally move the plurality of opposing paddles with respect to the deformable tube.

14. A method for use with a catheter assembly having an elongated catheter coaxially disposable within a sheath, the method comprising:

providing a medical device, the medical device comprising:

a deformable tube having a proximal end, a distal end, an outer wall with an outer diameter, and an inner wall forming an axial lumen, the distal end configured to attach to the sheath, the proximal end configured to receive the catheter into the lumen; and a plurality of opposing paddles disposed against the outer wall, each of the opposing paddles having a generally planar lock region configured to be disposed against outer wall at the outer diameter, the lock surface disposed tangentially to the deformable tube, the plurality of opposing paddles laterally movable with respect to the deformable tube along the outer diameter;

wherein the catheter is coaxially disposed within the sheath, releasably urging the opposing paddles against the deformable tube at the outer diameter to collapse the deformable tube to hold the catheter in place with respect to the sheath and deformable tube, the collapsed deformable tube to form an elongated opening along the inner wall and the catheter; and removing the catheter from the deformable tube and releasably urging the opposing paddles against the deformable tube at the outer diameter to collapse the deformable tube and seal the lumen.

15. The method of claim 14, and further including flowing a fluid into the elongated opening.

16. The method of claim 15, wherein providing the medical device includes providing the deformable tube having an inner wall with a circular cross section, and wherein holding the catheter in place with respect to the sheath includes ovalizing the cross section to form the elongated opening.

17. The method of claim 14, including forming an overlapping region on the deformable tube.

18. The method of claim 17, wherein holding the catheter in place with respect to the sheath includes pinching the catheter with the inner wall associated with the overlapping region.

19. The method of claim 17, wherein collapsing the deformable tube and sealing the lumen includes collapsing the deformable tube at the overlapping region.

20. The method of claim 14, wherein providing the medical device includes providing a proximal hub attached to the proximal end, and further including guiding the catheter into lumen via the proximal hub.

* * * * *